United States Patent [19]

Fischer

[11] 3,985,542

[45] Oct. 12, 1976

[54] HERBICIDE

[75] Inventor: Adolf Fischer, Mutterstadt, Germany

[73] Assignee: BASF Aktiengesellschaft, Ludwigshafen (Rhine), Germany

[22] Filed: Oct. 3, 1974

[21] Appl. No.: 511,942

[30] Foreign Application Priority Data
Oct. 19, 1973 Germany............................ 2352537

[52] U.S. Cl......................................... 71/88; 71/66; 71/67; 71/92; 71/100; 71/103; 71/106; 71/111; 71/113; 71/115
[51] Int. Cl.²............................................ A01N 9/00
[58] Field of Search......................... 71/90, 88, 92

[56] References Cited
UNITED STATES PATENTS

| | | | |
|---|---|---|---|
| 3,210,353 | 10/1965 | Reicheneder et al. | 71/92 |
| 3,689,507 | 9/1972 | Gates et al. | 71/88 |
| 3,849,107 | 11/1974 | Fischer | 71/121 |
| 3,861,900 | 1/1975 | Fischer | 71/121 |

FOREIGN PATENTS OR APPLICATIONS

| | | | |
|---|---|---|---|
| 1,419,362 | 12/1964 | France | 71/92 |
| 1,434,994 | 1/1965 | France | 71/92 |
| 2,324,592 | 12/1974 | Germany | 71/88 |

*Primary Examiner*—Glennon H. Hollrah
*Attorney, Agent, or Firm*—Johnston, Keil, Thompson & Shurtleff

[57] ABSTRACT

New and valuable herbicide comprising a composition of 2,3-dihydro-3,3-dimethyl-2-(alkoxy, allyloxy or propargyloxy) benzofuran-5-yl-methyl or dimethylamino sulfonate and 1-phenyl-4-amino-5-chloropyridazone-(6).

10 Claims, No Drawings

HERBICIDE

It is known that benzofuranylalkylamino sulfonates, pyridazones, carbamates, thiol carbamates, substituted fatty acids, uracils, pyrazolium sulfates and ethyl-N-benzoyl-N-(3,4-dichlorophenyl)-2-aminopropionate have a herbicidal action. However, this action is not always satisfactory.

I have now found that a composition of
a. a compound of the formula

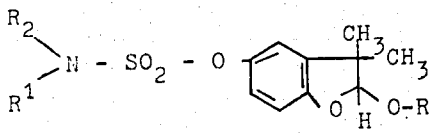

where R, $R^1$ and $R^2$ each denote hydrogen or an unsubstituted or alkoxy- or halogen-substituted aliphatic radical of a maximum of 4 carbon atoms, and
b. a compound of the formula

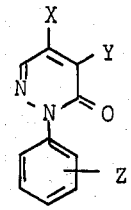

where X denotes amino, α-hydroxy-β,β,β-trichloroethylamino, acetylamino, haloacetylamino, acetoacetylamino, alkylamino, dialkylamino, alkoxyalkylamino, ester of adipamic acid, aminotartronic acid diethylester $(CH_3)_2N-CH=N$, alkoxy, or —NH—CD—COOR,
R denoting lower alkyl, phenyl or hydrogen, or a salt thereof, Y denotes chloro, bromo or methoxy and Z denotes hydrogen, halogen, methyl or trifluoromethyl, or
c. a compound of the formula

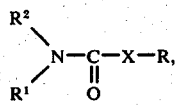

where $R^1$ denotes hydrogen or lower alkyl, $R^2$ denotes lower alkyl, unsubstituted or halogen-, methyl- or methoxy-substituted phenyl, aminobenzenesulfonyl, nitrobenzenesulfonyl, or a monocycloaliphatic, bicycloaliphatic or tricycloaliphatic radical, R denotes unsubstituted or halogen-substituted lower alkyl, alkenyl or alkynyl, unsubstituted or halogen- or alkyl-substituted phenyl or benzyl, the radical

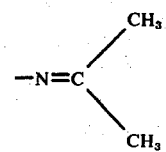

or

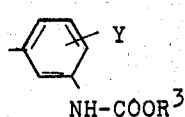

Y denoting methyl or hydrogen and $R^3$ denoting lower alkyl, and X denotes oxygen or sulfur, or
d. a compound of the formula

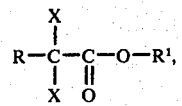

where X denotes hydrogen or halogen, R denotes alkyl, haloalkyl, benzamidooxy, unsubstituted benzyl, or benzyl substituted by halogen, methyl, methoxy or haloalkyl, and $R^1$ denotes unsubstituted or halogen-substituted alkyl or benzyl, or hydrogen, or a salt thereof, or
e. a compound of the formula

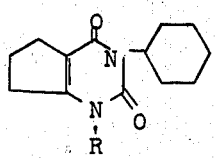

where R denotes hydrogen, α,α-dimethyl-β-acetoxypropionyl or acetyl, or
f. the compound

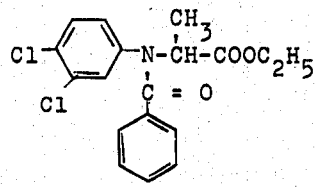

or
g. a compound of the formula

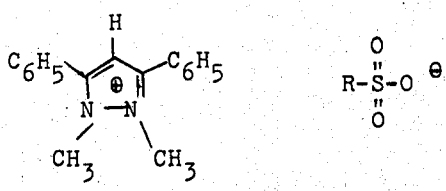

where R denotes alkoxy, unsubstituted phenyl, or phenyl substituted by halogen or lower alkyl, has a better herbicidal action than its components.

Preferred compositions are a+b, a+c, a+d, a+e, a+f, a+g, a+b+c, a+b+d, a+b+e, a+b+f, a+b+g, a+c+d, a+c+e, a+c+f, a+c+g, a+d+e, a+d+f, a+d+g, a+e+f, a+e+g and a+f+g.

The compositions may contain one or more compounds of the formula a and of the formulas b, c, d, e, f, and g.

The ratio of the active ingredients to each other may be selected at will, and is for instance from 0.1 to 10 parts by weight of a : 1 part by weight of b to g, preferably 0.3 to 3 parts by weight of a : 1 part by weight of b to g.

The amount used of the agents according to the invention may vary and depends in essence on the type of effect to be achieved; it is generally from 0.1 to 30 (and more), preferably from 0.2 to 6, kg per hectare of active ingredient. The agents according to the invention may be used once or several times before or after planting, before sowing, and before, during or after emergence of the crop plants and unwanted plants.

The compositions may also be used as total herbicides on ditches, aquatic areas, railroad tracks, and barren or waste land, etc.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredient (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compound such as substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts,
esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

*Gramineae*, such as
  *Cynodon spp.*    *Dactylis spp.*
  *Digitaria spp.*    *Avena spp.*
  *Echinochloa spp.*    *Bromus spp.*
  *Setaria spp.*    *Uniola spp.*
  *Panicum spp.*    *Poa spp.*
  *Alopecurus spp.*    *Leptochloa spp.*
  *Lolium spp.*    *Brachiaria spp.*
  *Sorghum spp.*    *Eleusine spp.*
  *Agropyron spp.*    *Cenchrus spp.*
  *Phalaris spp.*    *Eragrostis spp.*
  *Apera spp.*    *Phragmites communis*
  etc.;

*Cyperaceae*, such as
  *Carex spp.*    *Eleocharis spp.*
  *Cyperus spp.*    *Scirpus spp.*
  etc.;

dicotyledonous weeds, such as
*Malvaceae*, e.g.,
  *Abutilon theoprasti*    *Hibiscus spp.*
  *Sida spp.*    *Malva spp.*
  etc.;

*Compositae*, such as
  *Ambrosia spp.*    *Centaurea spp.*
  *Lactuca spp.*    *Tussilago spp.*
  *Senecio spp.*    *Lapsana communis*
  *Sonchus spp.*    *Tagetes spp.*
  *Xanthium spp.*    *Erigeron spp.*
  *Iva spp.*    *Anthemis spp.*
  *Galinsoga spp.*    *Matricaria spp.*
  *Taraxacum spp.*    *Artemisia spp.*
  *Chrysanthemum spp.*    *Bidens spp.*
  *Cirsium spp.*    etc.;

*Convolvulaceae*, such as
  *Convolvulus spp.*    *Cuscuta spp.*
  *Ipomoea spp.*    *Jaquemontia tamnifolia*
  etc.;

*Cruciferae*, such as
  *Barbarea vulgaris*    *Arabidopsis thaliana*
  *Brassica spp.*    *Descurainia spp.*
  *Capsella spp.*    *Draba spp.*
  *Sisymbrium spp.*    *Coronopus didymus*
  *Thlaspi spp.*    *Lepidium spp.*
  *Sinapis arvensis*    *Raphanus spp.*
  etc.;

*Geraniaceae*, such as
  *Erodium spp.*    *Geranium spp.*
  etc.;

*Portulacaceae*, such as
  *Portulaca spp.*    etc.;

*Primulaceae*, such as
  *Anagallis arvensis*    *Lysimachia spp.*
  etc.;

*Rubiaceae*, such as
  *Richardia app.*    *biodia spp.*
  *Galium spp.*

*Scrophulariaceae*, such as
  *Linaria spp.*    *Digitalis spp.*
  *Veronica spp.*    etc.;

*Solanaceae*, such as
  *Physalis spp.*    *Nicandra spp.*
  *Solanum spp.*    *Datura spp.*
  etc.;

*Urticaceae*, such as
  *Urtica spp.*

*Violaceae*, such as
  *Viola spp.*    etc.;

*Zygophyllaceae*, such as
  *Tribulus terrestris*    etc.;

*Euphorbiaceae*, such as
  *Mercurialis annua*    *Euphorbia spp.*

*Umbelliferae*, such as
  *Daucus carota*    *Ammi majus*
  *Aethusa cynapium*    etc.;

*Commelinaceae*, such as
  *Commelina spp.*    etc.;

| | |
|---|---|
| Labiatae, such as<br>Lamium spp.<br>etc.; | Galeopsis spp. |
| Leguminosae, such as<br>Medicago spp.<br>Trifolium spp.<br>Vicia spp.<br>etc.; | Sesbania exaltata<br>Cassia spp.<br>Lathyrus spp. |
| Plantaginaceae, such as<br>Plantago spp. | etc.; |
| Polygonaceae, such as<br>Polygonum spp.<br>Rumex spp. | Fagopyrum spp.<br>etc.; |
| Aizoaceae, such as<br>Mollugo verticillata | etc.; |
| Amaranthaceae, such as<br>Amaranthus spp. | etc.; |
| Boraginaceae, such as<br>Amsinckia spp.<br>Myostis spp.<br>etc.; | Anchusa spp.<br>Lithospermum spp. |
| Caryophyllaceae, such as<br>Stellaria spp.<br>Spergula spp.<br>Saponaria spp.<br>Scleranthus annuus | Silene spp.<br>Cerastium spp.<br>Agrostemma githago<br>etc.; |
| Chenopodiaceae, such as<br>Chenopodium spp.<br>Kochia spp.<br>Salsola Kali | Atriplex spp.<br>Monolepsis nuttalliana<br>etc.; |
| Lythraceae, such as<br>Cuphea spp. | etc.; |
| Oxalidaceae, such as<br>Oxalis spp. | |
| Ranunculaceae, such as<br>Ranunculus spp.<br>Delphinium spp. | Adonis spp.<br>etc.; |
| Papaveraceae, such as<br>Papaver spp.<br>etc.; | Fumaria officinalis |
| Onagraceae, such as<br>Jussiaea spp. | etc.; |
| Rosaceae, such as<br>Alchemillia spp.<br>etc.; | Potentilla spp. |
| Potamogetonaceae, such as<br>Potamogeton spp. | etc.; |
| Najadaceae, such as<br>Najas spp. | etc.; |
| Equisetaceae<br>Equisetum spp. | etc.; |
| Marsileaceae, such as<br>Marsilea quadrifolia | etc.; |
| Polypodiaceae,<br>Pteridium quilinum | |
| Alismataceae, such as<br>Alisma spp.<br>etc.; | Sagittaria sagittifolia |

The agents according to the invention may be employed in cereal crops such as

| | |
|---|---|
| Avena spp.<br>Triticum spp.<br>Hordeum spp.<br>Secale spp.<br>Saccharum officinarum | Sorghum<br>Zea mays<br>Panicum milaceum<br>Oryza spp. | and in dicotyledonous crops such as

| | |
|---|---|
| Cruciferae, e.g.<br>Brassica spp.<br>Sinapis spp. | Raphanus spp.<br>Lepidium spp. |
| Compositae, e.g.<br>Lactuca spp.<br>Helianthus spp. | Carthamus spp.<br>Scorzonera spp. |
| Malvaceae, e.g.<br>Gossypium hirsutum | |
| Leguminosae, e.g.<br>Medicago spp.<br>Trifolium spp.<br>Pisum spp. | Phaseolus spp.<br>Arachis spp.<br>Glycine max. |
| Chenopodium, e.g.<br>Beta vulgaris | Spinacia spp. |
| Solanaceae, e.g.<br>Solanum spp.<br>Nicotiania spp. | Capsicum annuum |
| Linaceae, e.g.<br>Linum spp. | |
| Umbelliferae, e.g.<br>Petroselinum spp.<br>Daucus carota | Apium graveolens |
| Rosaceae, e.g.<br>Fragaria | |
| Cucurbitaceae, e.g.<br>Cucumis spp. | Cucurbita spp. |
| Liliaceae, e.g.<br>Allium spp. | |
| Vitaceae, e.g.<br>Vitis vinifera | |
| Bromeliaceae, e.g.<br>Ananas sativus | |

In the greenhouse and in the open, compositions of the following compounds were tested on the above-mentioned plants. Their action corresponds to that of the compositions employed in Examples 1 to 11:

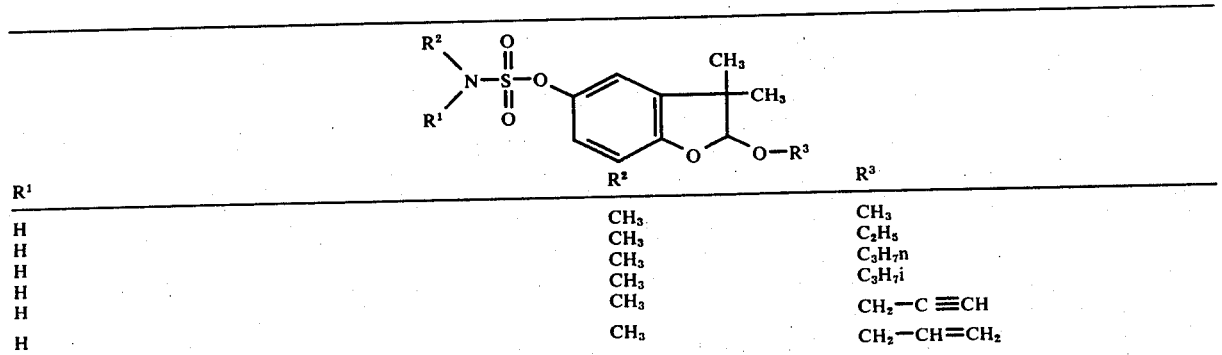

| R¹ | R² | R³ |
|---|---|---|
| H | CH₃ | CH₃ |
| H | CH₃ | C₂H₅ |
| H | CH₃ | C₃H₇-n |
| H | CH₃ | C₃H₇-i |
| H | CH₃ | CH₂—C≡CH |
| H | CH₃ | CH₂—CH=CH₂ |

-continued

| | | |
|---|---|---|
| H | C₂H₅ | CH₃ |
| H | C₂H₅ | C₂H₅ |
| H | C₃H₇n | CH₃ |
| H | C₂H₅ | C₃H₇n |
| H | C₂H₅ | C₃H₇i |
| H | C₃H₇n | C₂H₅ |
| H | C₃H₇n | C₃H₇n |
| H | C₃H₇n | C₃H₇i |
| H | C₃H₇i | CH₃ |
| H | C₃H₇i | C₂H₅ |
| H | C₃H₇i | C₃H₇n |
| H | C₃H₇i | C₃H₇i |
| CH₃ | CH₃ | CH₃ |
| CH₃ | CH₃ | CH₂—CH₂—Cl |
| CH₃ | CH₃ | C₂H₅ |
| CH₃ | CH₃ | CH₂—CH₂—OCH₃ |
| CH₃ | CH₃ | CH₂—CH=CH₂ |
| CH₃ | CH₃ | C₃H₇n |
| CH₃ | CH₃ | C₃H₇i |
| C₂H₅ | C₂H₅ | CH₃ |
| C₂H₅ | C₂H₅ | C₂H₅ |
| C₂H₅ | C₂H₅ | C₃H₇n |
| C₂H₅ | C₂H₅ | C₃H₇i |
| H | CH₃ | CH₂—CH₂Cl |

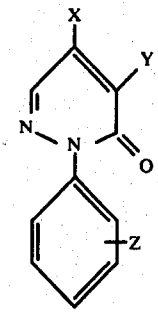

| X | Y | Z |
|---|---|---|
| NH₂ | Cl | H |
| NH—C(=O)—CH₃ | Cl | H |
| OCH₃ | Cl | H |
| NH₂ | Br | H |
| NH—CHOH—CCl₃ | Br | H |
| NH—C(=O)—CH₃ | Br | H |
| NH—C(=O)—CH₂Br | Br | H |
| NH—C(=O)—CH₂—C(=O)—CH₃ | Br | H |
| NH—COOC₄H₉ tert. | Br | H |
| NH—C(=O)—COOCH₃ | Br | H |
| NH—C(=O)—COOC₂H₅ | Br | H |
| NH—C(=O)—COOC₃H₇i | Br | H |
| NH—C(=O)—COOC₆H₅ | Br | H |
| NH—C(=O)—COONa | Br | H |
| NH—C(=O)—COOH · (CH₃)₂N—CH₂CH₂OH | Br | H |
| NH—C(=O)—CHCl₂ | Br | H |
| NH₂ | OCH₃ | H |
| OCH₃ | OCH₃ | H |
| OCH₃ | Br | H |

-continued

| | | |
|---|---|---|
| NH—C(=O)—(CH₂)₄—COOCH₃ | Br | H |
| NH—C(COOC₂H₅)(OH)(COOC₂H₅) | Br | H |
| NH₂ | Br | CH₃ |
| NH₂ | Cl | CH₃ |
| NH—C(=O)—COOC₄H₉ tert. | Br | CH₃ |
| OCH₃ | Br | CH₃ |
| OCH₃ | Cl | CH₃ |
| OCH₃ | OCH₃ | CH₃ |
| NH₂ | Cl | CF₃ |
| NH₂ | Br | CF₃ |
| NH—CHOH—CCl₃ | Br | CF₃ |
| NH—CHOH—CCl₃ | Cl | CF₃ |
| NH—C(=O)—CH₃ | Br | CF₃ |
| NH—C(=O)—CH₃ | Cl | CF₃ |
| NH—C(=O)—CH₂Cl | Cl | CF₃ |
| NH—C(=O)—CH₂Cl | Br | CF₃ |
| N(C₂H₅)(C₂H₅) | Cl | CF₃ |
| NH—C(=O)—COOC₂H₅ | Br | CF₃ |
| NH—C(=O)—COOH | Br | CF₃ |
| NH—C(=O)—COOH | Cl | CF₃ |
| NH—C(=O)—COOC₄H₉ tert. | Br | CF₃ |
| NH—C(=O)—COONa | Br | CF₃ |
| NH—C(=O)—CHCl₂ | Br | CF₃ |
| NH—CH₃ | Cl | CF₃ |
| N(CH₃)(CH₃) | Cl | CF₃ |
| N(CH₃)(CH₃) | Br | CF₃ |
| NH—C₂H₅ | Cl | CF₃ |
| OCH₃ | Cl | CF₃ |
| OCH₃ | Cl | CF₃ |
| OCH₃ | Br | CF₃ |
| OCH₃ | OCH₃ | CF₃ |
| N(OCH₃)(CH₃) | Cl | CF₃ |
| N(CH₃)(OCH₃) | Br | CF₃ |
| N=CH—N(CH₃)(CH₃) | Br | CF₃ |
| NH—OCH₃ | Cl | CF₃ |

-continued

| | | | |
|---|---|---|---|
| NH—OCH₃ | | Br | CF₃ |

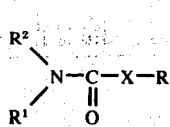

| R¹ | R² | X | R |
|---|---|---|---|
| H | CH₃ | O | 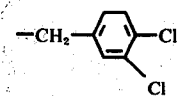 |
| H | CH₃ | O | $C_4H_9$ tert. 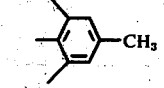 $C_4H_9$ tert. |
| H |  | O | $-C_3H_7$ i |
| H |  | O | 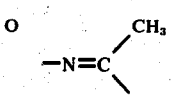 |
| H | $-SO_2-$$-NO_2$ | O | $-CH_3$ |
| H | $-SO_2-$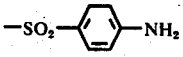$-NH_2$ | O | $CH_3$ |
| H | 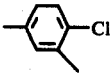 | O | $-CH_3$ |
| H | 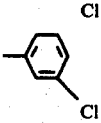 | O | $-C_3H_7$ i |
| H | 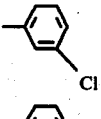 | O | $-CH_2-C\equiv C-CH_2Cl$ |
| H | 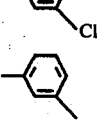 | O |  |
| H | 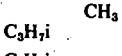 | O | 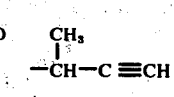 |
| $C_3H_7$i | $C_3H_7$i | S | $-CH_2-CCl=CHCl$ |
| $C_3H_7$i | $C_3H_7$i | S | $-CH_2-CCl=CCl_2$ |
| $C_3H_7$n | $C_3H_7$n | S | $-C_2H_5$ |
| $C_4H_9$n | $C_4H_9$n | S | $-C_2H_5$ |
| $C_4H_9$i | $C_4H_9$i | S | $-C_2H_5$ |
| $C_4H_9$n | $C_2H_5$ | S | $-C_3H_7$n |
| $C_3H_7$n | $C_3H_7$n | S | $-C_3H_7$n |
| $C_3H_7$n | $C_3H_7$n | S | $-C_4H_9$ tert. |
| $C_2H_5$ |  | S | $-C_2H_5$ |
| $-C_2H_5$ | $-C_2H_5$ | S | 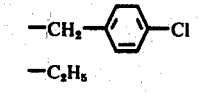 |
| $-CH_2-C\equiv CH$ |  | S | $-C_2H_5$ |
| $C_2H_5$ |  | S | $C_2H_5$ |
| $C_2H_5$ |  | S | $C_3H_7$i |

-continued

| | | S | CH₃ |
|---|---|---|---|
| C₂H₅ |  | | |
| C₂H₅ |  | S | C₂H₅ |
| C₂H₅ |  | S | C₂H₅ |

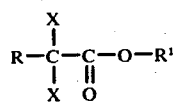

| R | X | X | R¹ |
|---|---|---|---|
| CH₃ | Cl | Cl | Na |
| CH₂Cl | Cl | Cl | Na |
| H | Cl | Cl | Na |
| Cl | Cl | Cl | Na |
| CH₃ | Cl | Cl | —CH₂—⌬ |
| CH₃ | Cl | Cl | —CH₂—CH₂—Cl |
| CH₃—CH₂— | Cl | Cl | Na |
| CHF₂ | F | F | Na |
|  | H | Cl | CH₃ |
| Cl—⌬—CH₂— | | | |
| ⌬—CO—NH—O— | H | H | H |

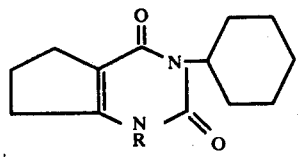

| R |
|---|
| H |
| —C—CH₃<br>‖<br>O |
| —C—C(CH₃)₂—CH₂—O—CO—CH₃<br>‖<br>O |

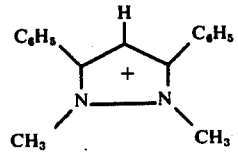 

| R |
|---|
| CH₃ |
| CH₃—⌬— |
| Cl—⌬(Cl)—N(—CH(CH₃)—COOC₂H₅)—CO—⌬ |

EXAMPLE 1

In the greenhouse, loamy sandy soil was filled into pots and sown with various seeds. The soil prepared in this manner was then treated with the following amounts of the following individual active ingredients and compositions thereof as emulsions or dispersions:

I. 2,3-dihydro-3,3-dimethyl-2-ethoxybenzofuran-5-ylmethylamino sulfonate

II. 2,3-dihydro-3,3-dimethyl-2-ethoxybenzofuran-5-yldimethylamino sulfonate

III. 1-phenyl-4-amino-5-chloropyridazone-(6)

V. ethyl N-ethyl-N-cyclohexylthiol carbamate

VI. 3-cyclohexyl-5,6-trimethylene uracil

XII. 2,3-dichloroallyl N,N-diisopropylthiol carbamate

XIII. 2,3,3-trichloroallyl N,N-diisopropylthiol carbamate

XIV. 2,3-dihydro-3,3-dimethyl-2-methoxybenzofuran-5-yldimethylamino sulfonate

XV. 2,3-dihydro-3,3-dimethyl-2-methoxybenzofuran-5-ylmethylamino sulfonate

I, II, VI, XIV and XV each at rates of 0.5, 0.75, 1 and 2 kg/ha and III, V, XII and XIII each at rates of 0.5, 1, 1.5 and 2 kg/ha I+III+V, I+III+VI, I+III+VII, I+III+VIII, II+III+V, II+III+VI, II+III+VII, II+III+VIII, XIV+III+V, XIV+III+VI, XIV+III+VII, XIV+III+VIII, XV+III+V, XV+III+VI, XV+III+VII and XV+III+VIII each at rates of 0.5+0.5+1, 0.5+1+0.5 and 1+0.5+0.5 kg/ha I+III, II+III, I+V and II+V each at rates of 0.5+1.5, 1.5+0.5 and 1+1 kg/ha I+VI and II+VI each at rates of 0.5+1, 1+0.5 and 0.75+0.75 kg/ha XIV+III, XV+III, XIV+V and XV+V each at rates of 0.5+1.5, 1.5+0.5 and 1+1 kg/ha XIV+VI and XV+VI each at rates of 0.5+1, 1+0.5 and 0.75+0.75 kg/ha I+XII, I+XIII, II+XII, II+XIII, XIV+XII, XIV+XIII, XV+XII and XV+XIII each at rates of 0.5+1.5, 1.5+0.5 and 1+1 kg/ha.

After 3 to 4 weeks it was ascertained that the compositions had a better herbicidal action than their components, combined with the same crop plant compatibility.

The results are given below:

| Active ingredient | I | | | | | II | | | | |
|---|---|---|---|---|---|---|---|---|---|---|
| kg/ha | 0.5 | 0.75 | 1 | 1.5 | 2 | 0.5 | 0.75 | 1 | 1.5 | 2 |
| Crop plants: | | | | | | | | | | |
| Beta vulgaris | 0 | 0 | 0 | 0 | 0 | 0 | 0 | 0 | 0 | 0 |
| Unwanted plants: | | | | | | | | | | |
| Avena fatua | 20 | 30 | 40 | 60 | 95 | 70 | 85 | 95 | 100 | 100 |
| Echinochloa-crus-galli | 10 | 20 | 30 | 37 | 58 | 70 | 80 | 90 | 100 | 100 |
| Galium aparine | 15 | 25 | 32 | 50 | 60 | 20 | 30 | 40 | 52 | 70 |
| Matricaria chamomilla | 7 | 15 | 30 | 35 | 40 | 5 | 15 | 20 | 30 | 50 |

0 = no damage
100 = complete destruction

| Active ingredient | III | | | | V | | | | VI | | | |
|---|---|---|---|---|---|---|---|---|---|---|---|---|
| kg/ha | 0.5 | 1 | 1.5 | 2 | 0.5 | 1 | 1.5 | 2 | 0.5 | 0.75 | 1 | 1.5 | 2 |
| Crop plants: | | | | | | | | | | | | |
| Beta vulgaris | 0 | 0 | 0 | 0 | 0 | 0 | 0 | 0 | 0 | 0 | 0 | 0 | 20 |
| Unwanted plants: | | | | | | | | | | | | |
| Avena fatua | 5 | 12 | 15 | 20 | 12 | 30 | 40 | 60 | 5 | 15 | 18 | 20 | 30 |
| Echinochloa crus-galli | 8 | 13 | 20 | 32 | 20 | 46 | 60 | 80 | 16 | 25 | 35 | 70 | 90 |
| Galium aparine | 15 | 40 | 50 | 75 | 0 | 10 | 15 | 20 | 10 | 30 | 50 | 60 | 75 |
| Matricaria chamomilla | 30 | 50 | 60 | 85 | 5 | 7 | 9 | 10 | 20 | 56 | 70 | 75 | 95 |

0 = no damage
100 = complete destruction

| Active ingredient | XII | | | | XIII | | | | XIV | | | |
|---|---|---|---|---|---|---|---|---|---|---|---|---|
| kg/ha | 0.5 | 1 | 1.5 | 2 | 0.5 | 1 | 1.5 | 2 | 0.5 | 0.75 | 1 | 1.5 | 2 |
| Crop plants: | | | | | | | | | | | | |
| Beta vulgaris | 0 | 0 | 0 | 10 | 0 | 0 | 0 | 7 | 0 | 0 | 0 | 0 | 0 |
| Unwanted plants: | | | | | | | | | | | | |
| Avena fatua | 20 | 60 | 83 | 95 | 30 | 67 | 90 | 98 | 70 | 80 | 90 | 100 | 100 |
| Echinochloa crus-galli | 16 | 30 | 40 | 50 | 15 | 38 | 50 | 60 | 70 | 80 | 90 | 100 | 100 |
| Galium aparine | 0 | 0 | 5 | 8 | 0 | 0 | 5 | 10 | 17 | 25 | 35 | 50 | 65 |
| Matricaria chamomilla | 5 | 10 | 13 | 19 | 9 | 12 | 15 | 21 | 5 | 10 | 20 | 28 | 45 |

0 = no damage
100 = complete destruction

| Active ingredient | XV | | | | | I+II+V | | | I+II+VI | | |
|---|---|---|---|---|---|---|---|---|---|---|---|
| | | | | | | 0.5 | 0.5 | 1 | 0.5 | 0.5 | 1 |
| | | | | | | 0.5 | 1 | 0.5 | 0.5 | 1 | 0.5 |
| kg/ha | 0.5 | 0.75 | 1 | 1.5 | 2 | 1 | 0.5 | 0.5 | 1 | 0.5 | 0.5 |
| Crop plants: | | | | | | | | | | | |
| Beta vulgaris | 0 | 0 | 0 | 0 | 0 | 0 | 0 | 0 | 0 | 0 | 0 |
| Avena fatua | 15 | 26 | 35 | 55 | 85 | 97 | 85 | 97 | 83 | 77 | 95 |
| Echinochloa crus-galli | 12 | 20 | 30 | 40 | 80 | 100 | 83 | 98 | 94 | 80 | 94 |
| Galium aparine | 10 | 20 | 30 | 40 | 50 | 80 | 93 | 84 | 100 | 100 | 97 |

-continued

| Active ingredient | XV | | | | | I+II+V | | | | I+II+VI | | |
|---|---|---|---|---|---|---|---|---|---|---|---|---|
| | | | | | | 0.5 | 0.5 | 1 | 0.5 | 0.5 | 1 | |
| | | | | | | 0.5 | 1 | 0.5 | 0.5 | 1 | 0.5 | |
| kg/ha | 0.5 | 0.75 | 1 | 1.5 | 2 | 1 | 0.5 | 0.5 | 1 | 0.5 | 0.5 | |
| *Matricaria chamomilla* | 12 | 20 | 36 | 45 | 60 | 86 | 100 | 100 | 100 | 100 | 100 | |

0 = no damage
100 = complete destruction

| Active ingredient | I+III+XII | | | I+III+XIII | | | II+III+V | | | II+III+VI | | |
|---|---|---|---|---|---|---|---|---|---|---|---|---|
| | 0.5 | 0.5 | 1 | 0.5 | 0.5 | 1 | 0.5 | 0.5 | 1 | 0.5 | 0.5 | 1 |
| | 0.5 | 1 | 0.5 | 0.5 | 1 | 0.5 | 0.5 | 1 | 0.5 | 0.5 | 1 | 0.5 |
| kg/ha | 1 | 0.5 | 0.5 | 1 | 0.5 | 0.5 | 1 | 0.5 | 0.5 | 1 | 0.5 | 0.5 |
| Crop plants: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 100 | 95 | 100 | 100 | 100 | 100 | 100 | 100 | 100 | 100 | 100 | 100 |
| *Echinochloa crus-galli* | 88 | 80 | 94 | 94 | 80 | 91 | 100 | 100 | 100 | 100 | 100 | 100 |
| *Galium aparine* | 75 | 96 | 86 | 75 | 95 | 85 | 83 | 100 | 91 | 100 | 100 | 100 |
| *Matricaria chamomilla* | 87 | 100 | 100 | 89 | 100 | 100 | 85 | 100 | 92 | 100 | 100 | 100 |

0 = no damage
100 = complete destruction

| Active ingredient | II+III+XII | | | II+III+XIII | | | XIV+III+V | | | XIV+III+VI | | |
|---|---|---|---|---|---|---|---|---|---|---|---|---|
| | 0.5 | 0.5 | 1 | 0.5 | 0.5 | 1 | 0.5 | 0.5 | 1 | 0.5 | 0.5 | 1 |
| | 0.5 | 1 | 0.5 | 0.5 | 1 | 0.5 | 0.5 | 1 | 0.5 | 0.5 | 1 | 0.5 |
| kg/ha | 1 | 0.5 | 0.5 | 1 | 0.5 | 0.5 | 1 | 0.5 | 0.5 | 1 | 0.5 | 0.5 |
| Crop plants: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 100 | 100 | 100 | 100 | 100 | 100 | 100 | 100 | 100 | 100 | 100 | 100 |
| *Echinochloa crus-gali* | 100 | 100 | 100 | 100 | 100 | 100 | 100 | 100 | 100 | 100 | 100 | 100 |
| *Galium aparine* | 76 | 98 | 93 | 75 | 98 | 75 | 79 | 96 | 87 | 100 | 100 | 100 |
| *Matricaria chamomilla* | 85 | 95 | 94 | 87 | 100 | 85 | 80 | 100 | 94 | 100 | 100 | 100 |

0 = no damage
100 = complete destruction

| Active ingredient | XIV+III+XII | | | XIV+III+XIII | | | XV+III+V | | | XV+III+VI | | |
|---|---|---|---|---|---|---|---|---|---|---|---|---|
| | 0.5 | 0.5 | 1 | 0.5 | 0.5 | 1 | 0.5 | 0.5 | 1 | 0.5 | 0.5 | 1 |
| | 0.5 | 1 | 0.5 | 0.5 | 1 | 0.5 | 0.5 | 1 | 0.5 | 0.5 | 1 | 0.5 |
| kg/ha | 1 | 0.5 | 0.5 | 1 | 0.5 | 0.5 | 1 | 0.5 | 0.5 | 1 | 0.5 | 0.5 |
| Crop plants: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 100 | 100 | 100 | 100 | 100 | 100 | 90 | 80 | 92 | 80 | 72 | 95 |
| *Echinochloa crus-galli* | 100 | 100 | 100 | 100 | 100 | 100 | 100 | 85 | 96 | 95 | 82 | 94 |
| *Galium aparine* | 75 | 95 | 87 | 76 | 96 | 88 | 75 | 87 | 85 | 100 | 100 | 96 |
| *Matricaria chamomilla* | 85 | 100 | 95 | 87 | 100 | 98 | 89 | 100 | 100 | 100 | 100 | 100 |

0 = no damage
100 = complete destruction

| Active ingredient | XV+III+XII | | | XV+III+XIII | | | I+III | | | II+III | | |
|---|---|---|---|---|---|---|---|---|---|---|---|---|
| | 0.5 | 0.5 | 1 | 0.5 | 0.5 | 1 | | | | | | |
| | 0.5 | 1 | 0.5 | 0.5 | 1 | 0.5 | 0.5 | 1.5 | 1 | 0.5 | 1.5 | 1 |
| kg/ha | 1 | 0.5 | 0.5 | 1 | 0.5 | 0.5 | 1.5 | 0.5 | 1 | 1.5 | 0.5 | 1 |
| Crop plants: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 100 | 85 | 100 | 100 | 100 | 100 | 79 | 100 | 95 | 100 | 100 | 100 |
| *Echinochloa crus-galli* | 88 | 82 | 94 | 100 | 80 | 93 | 74 | 84 | 83 | 100 | 100 | 100 |
| *Galium aparine* | 67 | 90 | 83 | 70 | 90 | 85 | 100 | 100 | 100 | 100 | 100 | 100 |

-continued

| Active ingredient | XV+III+XII | | | XV+III+XIII | | | I+III | | | II+III | | |
|---|---|---|---|---|---|---|---|---|---|---|---|---|
| kg/ha | 0.5 | 0.5 | 1 | 0.5 | 0.5 | 1 | 0.5 | 1.5 | 1 | 0.5 | 1.5 | 1 |
| | 0.5 | 1 | 0.5 | 0.5 | 1 | 0.5 | 1.5 | 0.5 | 1 | 1.5 | 0.5 | 1 |
| | 1 | 0.5 | 0.5 | 1 | 0.5 | 0.5 | 1.5 | 0.5 | 1 | 1.5 | 0.5 | 1 |
| Matricaria chamomilla | 92 | 100 | 100 | 91 | 100 | 100 | 100 | 100 | 100 | 100 | 100 | 100 |

0 = no damage
100 = complete destruction

| Active ingredient | I+V | | | II+V | | | I+VI | | | II+VI | | |
|---|---|---|---|---|---|---|---|---|---|---|---|---|
| kg/ha | 0.5 | 1.5 | 1 | 0.5 | 1.5 | 1 | 0.5 | 1 | 0.75 | 0.5 | 1 | 0.75 |
| | 1.5 | 0.5 | 1 | 1.5 | 0.5 | 1 | 1 | 0.5 | 0.75 | 1 | 0.5 | 0.75 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 98 | 100 | 100 | 100 | 100 | 100 | 82 | 87 | 88 | 100 | 100 | 100 |
| Echinochloa crus-galli | 100 | 95 | 100 | 100 | 100 | 100 | 90 | 90 | 89 | 100 | 100 | 100 |
| Galium aparine | 70 | 86 | 82 | 75 | 89 | 85 | 100 | 81 | 94 | 100 | 100 | 100 |
| Matricaria chamomilla | 56 | 80 | 76 | 54 | 73 | 66 | 100 | 95 | 100 | 100 | 100 | 100 |

0 = no damage
100 = complete destruction

| Active ingredient | XIV+III | | | XV+III | | | XIV+V | | | XV+V | | |
|---|---|---|---|---|---|---|---|---|---|---|---|---|
| kg/ha | 0.5 | 1.5 | 1 | 0.5 | 1.5 | 1 | 0.5 | 1.5 | 1 | 0.5 | 1.5 | 1 |
| | 1.5 | 0.5 | 1 | 1.5 | 0.5 | 1 | 1.5 | 0.5 | 1 | 1.5 | 0.5 | 1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 72 | 98 | 86 | 100 | 100 | 100 | 95 | 100 | 100 |
| Echinochloa crus-galli | 100 | 100 | 100 | 75 | 86 | 83 | 100 | 100 | 100 | 100 | 100 | 100 |
| Galium aparine | 100 | 100 | 100 | 98 | 93 | 100 | 72 | 87 | 81 | 65 | 78 | 77 |
| Matricaria chamomilla | 100 | 98 | 100 | 100 | 100 | 100 | 54 | 70 | 65 | 60 | 87 | 81 |

0 = no damage
100 = complete destruction

| Active ingredient | XIV+VI | | | XV+VI | | | I+XII | | | I+XIII | | |
|---|---|---|---|---|---|---|---|---|---|---|---|---|
| kg/ha | 0.5 | 1 | 0.75 | 0.5 | 1 | 0.75 | 0.5 | 1.5 | 1 | 0.5 | 1.5 | 1 |
| | 1 | 0.5 | 0.75 | 1 | 0.5 | 0.75 | 1.5 | 0.5 | 1 | 1.5 | 0.5 | 1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 78 | 85 | 86 | 100 | 100 | 100 | 100 | 100 | 100 |
| Echinochloa crus-galli | 100 | 100 | 100 | 90 | 86 | 90 | 90 | 91 | 95 | 96 | 90 | 100 |
| Galium aparine | 100 | 82 | 91 | 98 | 80 | 86 | 62 | 86 | 70 | 63 | 87 | 70 |
| Matricaria chamomilla | 100 | 84 | 100 | 100 | 97 | 100 | 59 | 78 | 79 | 61 | 83 | 78 |

0 = no damage
100 = complete destruction

| Active ingredient | II+XII | | | II+XIII | | | XIV+XII | | | XIV+XIII | | |
|---|---|---|---|---|---|---|---|---|---|---|---|---|
| kg/ha | 0.5 | 1.5 | 1 | 0.5 | 1.5 | 1 | 0.5 | 1.5 | 1 | 0.5 | 1.5 | 1 |
| | 1.5 | 0.5 | 1 | 1.5 | 0.5 | 1 | 1.5 | 0.5 | 1 | 1.5 | 0.5 | 1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Galium aparine | 65 | 100 | 80 | 70 | 90 | 78 | 65 | 90 | 75 | 65 | 90 | 75 |
| Matricaria chamomilla | 58 | 72 | 66 | 60 | 74 | 68 | 58 | 70 | 70 | 60 | 77 | 72 |

0 = no damage
100 = complete destruction

| Active ingredient | XV+XII | | | XV+XIII | | |
|---|---|---|---|---|---|---|
| kg/ha | 0.5 / 1.5 | 1.5 / 0.5 | 1 / 1 | 0.5 / 1.5 | 1.5 / 0.5 | 1 / 1 |
| Crop plants: | | | | | | |
| Beta vulgaris | 0 | 0 | 0 | 0 | 0 | 0 |
| Unwanted plants: | | | | | | |
| Avena fatua | 100 | 100 | 100 | 75 | 100 | 93 |
| Echinochloa crus-galli | 92 | 96 | 100 | 100 | 94 | 100 |
| Galium aparine | 55 | 81 | 70 | 100 | 90 | 100 |
| Matricaria chamomilla | 66 | 89 | 85 | 100 | 100 | 100 |

0 = no damage
100 = complete destruction

EXAMPLE 2

In the greenhouse, loamy sandy soil was filled into pots and sown with various seeds. The soil prepared in this manner was then treated with the following amounts of the following individual active ingredients and compositions thereof as granules:

I. 2,3-dihydro-3,3-dimethyl-2-ethoxybenzofuran-5-ylmethylamino sulfonate
II. 2,3-dihydro-3,3-dimethyl-2-ethoxybenzofuran-5-yldimethylamino sulfonate
III. 1-phenyl-4-amino-5-chloropyridazone-(6)
V. ethyl N-ethyl-N-cyclohexylthio carbamate
VI. 3-cyclohexyl-5,6-trimethylene uracil
XII. 2,3-dichloroallyl N,N-diisopropylthiol carbamate
XIII. 2,3,3-trichloroally N,N-diisopropylthiol carbamate
XIV. 2,3-dihydro-3,3-dimethyl-2-methoxybenzofuran-5-yldimethylamino sulfonate
XV. 2,3-dihydro-3,3-dimethyl-2-methoxybenzofuran-5-ylmethylamino sulfonate I, II, III and XIII each at rates of 1, 1.5, 2, 3, 4 and 4.5 kg/ha,
VI, XII, XIV and XV each at rates of 1, 1.5, 2, 3 and 4 kg/ha I+III+V, I+III+VI and I+III+XII each at rates of 1+1+2, 1+2+1 and 2+1+1 kg/ha I+III+XIII at rates of 1+1+2, 1+2+1, 2+1+1 and 2+1.5+1 kg/ha II+III+V, II+III+VI and II+III+XII each at rates of 1+1+2, 1+2+1 and 2+1+1 kg/ha II+III+XIII at rates of 1+1+2, 1+2+1, 2+1+1 and 2+1.5+1 kg/ha XIV+III+XV, XIV+III+VI, XIV+III+XII, XIV+III+XIII, XV+III+V, XV+III+VI, XV+III+XII and XV+III+XIII each at rates of 1+1+2, 1+2+1, and 2+1+1 kg/ha
I+III, II+III, I+V and II+V each at rates of 2+1, 1+2 and 2+2 kg/ha
I+VI and II+VI each at rates of 1.5+1.5, 1+2 and 2+1 kg/ha XIV+III, XV+III and XIV+V each at rates of 2+1, 1+2 and 2+2 kg/ha
XIV+VI and XV+VI each at rates of 1.5+1.5, 1+2 and 2+1 kg/ha I+XII, I+XIII II+XII, II+XIII. XIV+XIII, XIV+XIII, XV+XII and XV+XIII each at rates of 1.5+1.5, 2+1 and 1+2 kg/ha and, for comparison
XI 2-chloro-4,6-diethylamino-1,3,5-triazine at rates of 2 and 3 kg/ha
I+XI at a rate of 1+2 kg/ha.

| Active ingredient | I | | | | | | II | | | | | |
|---|---|---|---|---|---|---|---|---|---|---|---|---|
| kg/ha | 1 | 1.5 | 2 | 3 | 4 | 4.5 | 1 | 1.5 | 2 | 3 | 4 | 4.5 |
| Crop plants: | | | | | | | | | | | | |
| Beta vulgaris | 0 | 0 | 0 | 0 | 7 | 10 | 0 | 0 | 0 | 5 | 10 | 12 |
| Unwanted plants: | | | | | | | | | | | | |
| Avena fatua | 40 | 60 | 95 | 100 | 100 | 100 | 95 | 100 | 100 | 100 | 100 | 100 |
| Echinochloa crus-galli | 30 | 37 | 58 | 70 | 80 | 90 | 90 | 100 | 100 | 100 | 100 | 100 |
| Galium aparine | 32 | 50 | 60 | 75 | 90 | 98 | 40 | 52 | 70 | 80 | 95 | 100 |
| Matricaria chamomilla | 30 | 35 | 40 | 60 | 80 | 95 | 20 | 30 | 50 | 70 | 92 | 100 |

0 = no damage
100 = complete destruction

| Active ingredient | III | | | | | | V | | | | |
|---|---|---|---|---|---|---|---|---|---|---|---|
| kg/ha | 1 | 1.5 | 2 | 3 | 4 | 4.5 | 1 | 1.5 | 2 | 3 | 4 |
| Crop plants: | | | | | | | | | | | |
| Beta vulgaris | 0 | 0 | 0 | 0 | 0 | 0 | 0 | 0 | 0 | 0 | 10 |
| Unwanted plants: | | | | | | | | | | | |
| Avena fatua | 12 | 15 | 20 | 40 | 75 | 85 | 30 | 40 | 60 | 95 | 100 |
| Echinochloa crus-galli | 13 | 20 | 32 | 65 | 75 | 80 | 46 | 60 | 80 | 95 | 100 |
| Galium aparine | 40 | 50 | 75 | 90 | 98 | 100 | 10 | 15 | 20 | 47 | 60 |
| Matricaria chamomilla | 50 | 60 | 85 | 100 | 100 | 100 | 7 | 9 | 10 | 16 | 48 |

0 = no damage
100 = complete destruction

| Active ingredient | VI | | | | | XII | | | |
|---|---|---|---|---|---|---|---|---|---|
| kg/ha | 1 | 1.5 | 2 | 3 | 4 | 1 | 1.5 | 2 | 3 | 4 |
| Crop plants: | | | | | | | | | | |
| Beta vulgaris | 0 | 0 | 20 | 40 | 50 | 0 | 0 | 10 | 15 | 25 |
| Unwanted plants | | | | | | | | | | |
| Avena fatua | 18 | 20 | 30 | 70 | 90 | 60 | 83 | 95 | 100 | 100 |
| Echinochloa crus-galli | 35 | 70 | 90 | 100 | 100 | 30 | 40 | 50 | 80 | 90 |
| Galium aparine | 50 | 60 | 75 | 95 | 100 | 0 | 5 | 8 | 10 | 15 |

-continued

| Active ingredient | VI | | | | | XII | | | | |
|---|---|---|---|---|---|---|---|---|---|---|
| kg/ha | 1 | 1.5 | 2 | 3 | 4 | 1 | 1.5 | 2 | 3 | 4 |
| Matricaria chamomilla | 70 | 75 | 95 | 100 | 100 | 10 | 13 | 19 | 30 | 40 |

0 = no damage
100 = complete destruction

| Active ingredient | XIII | | | | | | XIV | | | | |
|---|---|---|---|---|---|---|---|---|---|---|---|
| kg/ha | 1 | 1.5 | 2 | 3 | 4 | 4.5 | 1 | 1.5 | 2 | 3 | 4 |
| Crop plants: | | | | | | | | | | | |
| Beta vulgaris | 0 | 0 | 7 | 10 | 20 | 28 | 0 | 0 | 0 | 4 | 10 |
| Unwanted plants: | | | | | | | | | | | |
| Avena fatua | 67 | 90 | 98 | 100 | 100 | 100 | 90 | 100 | 100 | 100 | 100 |
| Echinochloa crus-galli | 38 | 50 | 60 | 90 | 96 | 98 | 90 | 100 | 100 | 100 | 100 |
| Galium aparine | 0 | 5 | 10 | 14 | 20 | 24 | 35 | 50 | 65 | 75 | 90 |
| Matricaria chamomilla | 12 | 15 | 21 | 32 | 45 | 50 | 20 | 28 | 45 | 65 | 85 |

0 = no damage
100 = complete destruction

| Active ingredient | XV | | | | | I+III+V | | | I+III+VI | | |
|---|---|---|---|---|---|---|---|---|---|---|---|
| kg/ha | 1 | 1.5 | 2 | 3 | 4 | 1<br>1<br>2 | 1<br>2<br>1 | 2<br>1<br>1 | 1<br>1<br>2 | 1<br>2<br>1 | 2<br>1<br>1 |
| Crop plants: | | | | | | | | | | | |
| Beta vulgaris | 0 | 0 | 0 | 0 | 5 | 0 | 0 | 0 | 20 | 0 | 0 |
| Unwanted plants: | | | | | | | | | | | |
| Avena fatua | 35 | 55 | 85 | 98 | 100 | 100 | 100 | 100 | 100 | 100 | 100 |
| Echinochloa crus-galli | 30 | 40 | 80 | 95 | 100 | 100 | 100 | 100 | 100 | 100 | 100 |
| Galium aparine | 30 | 40 | 50 | 70 | 90 | 100 | 100 | 100 | 100 | 100 | 100 |
| Matricaria chamomilla | 36 | 45 | 60 | 80 | 95 | 100 | 100 | 100 | 100 | 100 | 100 |

0 = no damage
100 = complete destruction

| Active ingredient | I+II+XII | | | I+III+XII | | | II+III+V | | | II+III+VI | | |
|---|---|---|---|---|---|---|---|---|---|---|---|---|
| kg/ha | 1<br>1<br>2 | 1<br>2<br>1 | 2<br>1<br>1 | 1<br>1<br>2 | 1<br>2<br>1 | 2<br>1<br>1 | 2<br>1.5<br>1 | 1<br>1<br>2 | 1<br>2<br>1 | 2<br>1<br>1 | 1<br>1<br>2 | 1<br>2<br>1 | 2<br>1<br>1 |
| Crop plants: | | | | | | | | | | | | | |
| Beta vulgaris | 10 | 0 | 0 | 7 | 0 | 0 | 0 | 0 | 0 | 0 | 20 | 0 | 0 |
| Unwanted plants: | | | | | | | | | | | | | |
| Avena fatua | 100 | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 | 100 |
| Galium aparine | 100 | 100 | 100 | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 | 100 | 100 | 100 |

0 = no damage
100 = complete destruction

| Active ingredient | II+III+XII | | | II+III+XIII | | | XIV+III+V | | | XIV+III+VI | | |
|---|---|---|---|---|---|---|---|---|---|---|---|---|
| kg/ha | 1<br>1<br>2 | 1<br>2<br>1 | 2<br>1<br>1 | 1<br>1<br>2 | 1<br>2<br>1 | 2<br>1<br>1 | 2<br>1.5<br>1 | 1<br>1<br>2 | 1<br>2<br>1 | 2<br>1<br>1 | 1<br>1<br>2 | 1<br>2<br>1 | 2<br>1<br>1 |
| Crop plants: | | | | | | | | | | | | | |
| Beta vulgaris | 10 | 0 | 0 | 7 | 0 | 0 | 0 | 0 | 0 | 0 | 20 | 0 | 0 |
| Unwanted plants: | | | | | | | | | | | | | |
| Avena fatua | 100 | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 | 100 |
| Galium aparine | 100 | 100 | 100 | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 | 100 | 100 | 100 |

0 = no damage
100 = complete destruction

| Active ingredient | XIV+III+XII | | | XIV+III+XIII | | | XV+III+V | | | XV+III+VI | | |
|---|---|---|---|---|---|---|---|---|---|---|---|---|
| | 1 | 1 | 2 | 1 | 1 | 2 | 1 | 1 | 2 | 1 | 1 | 2 |
| | 1 | 2 | 1 | 1 | 2 | 1 | 1 | 2 | 1 | 1 | 2 | 1 |
| kg/ha | 2 | 1 | 1 | 2 | 1 | 1 | 2 | 1 | 1 | 2 | 1 | 1 |
| Crop plants: | | | | | | | | | | | | |
| Beta vulgaris | 10 | 0 | 0 | 7 | 0 | 0 | 0 | 0 | 0 | 20 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Galium aparine | 100 | 100 | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 | 100 | 100 |

0 = no damage
100 = complete destruction

| Active ingredient | XV+III+XII | | | XV+III+XIII | | | I+III | | | II+III | | |
|---|---|---|---|---|---|---|---|---|---|---|---|---|
| | 1 | 1 | 2 | 1 | 1 | 2 | | | | | | |
| | 1 | 2 | 1 | 1 | 2 | 1 | 2 | 1 | 2 | 2 | 1 | 2 |
| kg/ha | 2 | 1 | 1 | 2 | 1 | 1 | 1 | 2 | 2 | 1 | 2 | 2 |
| Crop plants: | | | | | | | | | | | | |
| Beta vulgaris | 10 | 0 | 0 | 7 | 0 | 0 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Echinochloa crus-galli | 100 | 100 | 100 | 100 | 100 | 100 | 79 | 82 | 98 | 100 | 100 | 100 |
| Galium aparine | 100 | 100 | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 | 100 | 100 |

0 = no damage
100 = complete destruction

| Active ingredient | I+V | | | II+V | | | I+VI | | | II+VI | | |
|---|---|---|---|---|---|---|---|---|---|---|---|---|
| | 2 | 1 | 2 | 2 | 1 | 2 | 1.5 | 1 | 2 | 1.5 | 1 | 2 |
| kg/ha | 1 | 2 | 2 | 1 | 2 | 2 | 1.5 | 2 | 1 | 1.5 | 2 | 1 |
| Crop plants: | | | | | | | | | | | | |
| Beta vulgaris | 0 | 0 | 0 | 0 | 0 | 0 | 0 | 20 | 0 | 0 | 20 | 0 |
| Unwanted plants: | | | | | | | | | | | | |
| Avena fatua | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 98 | 100 | 100 | 100 | 100 |
| Galium aparine | 100 | 92 | 100 | 100 | 96 | 100 | 100 | 100 | 100 | 100 | 100 | 100 |
| Matricaria chamomilla | 96 | 95 | 100 | 100 | 85 | 100 | 100 | 100 | 100 | 100 | 100 | 100 |

0 = no damage
100 = complete destruction

| Active ingredient | XIV+III | | | XV+III | | | XIV+V | | | XV+V | | |
|---|---|---|---|---|---|---|---|---|---|---|---|---|
| | 2 | 1 | 2 | 2 | 1 | 2 | 2 | 1 | 2 | 2 | 1 | 2 |
| kg/ha | 1 | 2 | 2 | 1 | 2 | 2 | 1 | 2 | 2 | 1 | 2 | 2 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 100 | 98 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Galium aparine | 100 | 100 | 100 | 100 | 100 | 100 | 100 | 94 | 100 | 100 | 92 | 100 |
| Matricaria chamomilla | 100 | 100 | 100 | 100 | 100 | 100 | 100 | 87 | 100 | 100 | 100 | 100 |

0 = no damage
100 = complete destruction

| Active ingredient | XIV+VI | | | XV+VI | | | I+XII | | | | I+XIII | | | |
|---|---|---|---|---|---|---|---|---|---|---|---|---|---|---|
| | 1.5 | 1 | 2 | 1.5 | 1 | 2 | 1.5 | 2 | 1 | 2 | 1.5 | 2 | 1 | 2 |
| kg/ha | 1.5 | 2 | 1 | 1.5 | 2 | 1 | 1.5 | 1 | 2 | 2 | 1.5 | 1 | 2 | 2 |
| Crop plants: | | | | | | | | | | | | | | |
| Beta vulgaris | 0 | 20 | 0 | 0 | 20 | 0 | 0 | 0 | 10 | 10 | 0 | 7 | 7 | |
| Unwanted plants: | | | | | | | | | | | | | | |
| Avena fatua | 100 | 100 | 100 | 100 | 100 | 100 | 100 | 100 | 100 | 100 | 100 | 100 | 100 | 100 |
| Enchinochloa crus-galli | 100 | 100 | 100 | 100 | 100 | 100 | 100 | 98 | 97 | 100 | 100 | 100 | 100 | 100 |
| Galium aparine | 100 | 100 | 100 | 100 | 100 | 100 | 94 | 97 | 84 | 100 | 93 | 97 | 87 | 100 |

-continued

| Active ingredient | XIV+VI | | | | XV+VI | | | | I+XII | | | | I+XIII | | | |
|---|---|---|---|---|---|---|---|---|---|---|---|---|---|---|---|---|
| kg/ha | 1.5<br>1.5 | 1<br>2 | 2<br>1 | 1.5<br>1.5 | 1<br>2 | 2<br>1 | 1.5<br>1.5 | 2<br>1 | 1<br>2 | 2<br>2 | 1.5<br>1.5 | 2<br>1 | 1<br>2 | 2<br>2 | | |
| Matricaria chamomilla | 100 | 100 | 100 | 100 | 100 | 100 | 87 | 90 | 87 | 96 | 90 | 91 | 90 | 100 | | |

0 = no damage
100 = complete destruction

| Active ingredient | II+XII | | | | II+XIII | | | | XIV+XII | | | |
|---|---|---|---|---|---|---|---|---|---|---|---|---|
| kg/ha | 1.5<br>1.5 | 2<br>1 | 1<br>2 | 2<br>2 | 1.5<br>1.5 | 2<br>1 | 1<br>2 | 2<br>2 | 1.5<br>1.5 | 2<br>1 | 1<br>2 | 2<br>2 |
| Crop plants: | | | | | | | | | | | | |
| Beta vulgaris | 0 | 0 | 10 | 10 | 0 | 0 | 7 | 7 | 0 | 0 | 10 | 10 |
| Unwanted plants: | | | | | | | | | | | | |
| Avena Fatua | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Galium aparine | 97 | 100 | 85 | 100 | 97 | 100 | 93 | 100 | 92 | 100 | 81 | 100 |
| Matricaria chamomilla | 86 | 100 | 77 | 100 | 88 | 100 | 84 | 100 | 79 | 93 | 76 | 100 |

0 = no damage
100 = complete destruction

| Active ingredient | XIV+XIII | | | | XV+XII | | | | XV+XIII | | | |
|---|---|---|---|---|---|---|---|---|---|---|---|---|
| kg/ha | 1.5<br>1.5 | 2<br>1 | 1<br>2 | 2<br>2 | 1.5<br>1.5 | 2<br>1 | 1<br>2 | 2<br>2 | 1.5<br>1.5 | 2<br>1 | 1<br>2 | 2<br>2 |
| Crop plants: | | | | | | | | | | | | |
| Beta vulgaris | 0 | 0 | 7 | 7 | 0 | 0 | 10 | 10 | 0 | 0 | 7 | 7 |
| Unwanted plants: | | | | | | | | | | | | |
| Avena fatua | 100 | 100 | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 | 100 | 100 |
| Galium aparine | 91 | 100 | 83 | 100 | 80 | 87 | 77 | 97 | 85 | 96 | 80 | 100 |
| Matricaria chamomilla | 80 | 94 | 79 | 100 | 95 | 100 | 91 | 100 | 100 | 100 | 96 | 100 |

0 = no damage
100 = complete destruction

| Active ingredient | XI | | I+XI |
|---|---|---|---|
| kg/ha | 2 | 3 | 1<br>2 |
| Crop plants: | | | |
| Beta vulgaris | 100 | 100 | 100 |
| Unwanted plants: | | | |
| Avena fatua | 95 | 100 | 100 |
| Echinochloa crus-galli | 50 | 65 | 100 |
| Galium aparaine | 30 | 35 | 90 |
| Matricaria chamomilla | 100 | 100 | 100 |

0 = no damage
100 = complete destruction

In the open, various plants were treated at a growth height of from 2 to 16 cm with the following amounts of the following individual active ingredients and compositions thereof as tankmix emulsions or dispersions:

I. 2,3-dihydro-3,3-dimethyl-2-ethoxybenzofuran-5-ylmethyl-amino sulfonate

II. 2,3-dihydro-3,3-dimethyl-2-ethoxybenzofuran-5-yldimethyl amino sulfonate

III. 1-phenyl-4-amino-5-chloropyridazone-(6)

IV. 3-methoxycarbonylaminophenyl-N-(3'-methylphenyl)-carbamate

V. ethyl N-ethyl-N-cyclohexylthiol carbamate

VI. 3-cyclohexyl-5,6-trimethylene uracil

VII. 1,2-dimethyl-3,5-diphenylpyrazolium methyl sulfate.

VIII. ethyl-N-benzoyl-N-(3,4-dichlorophenyl)-2-aminopropionate

IX. 4-chlorobutyn-2-yl-1 N-3-chlorophenylcarbamate

X. methhyl d-chloro-β-(4-chlorophenyl)-propionate

XIV. 2,3-dihydro-3,3-dimethyl-2-methoxybenzofuran-5-yldimethylamino sulfonate

XV. 2,3-dihydro-3,3-dimethyl-2-methoxybenzofuran-5-ylmethylamino sulfonate each at rates of 0.5 1, 1.5 and 2kg/ha I+III, I+IV, I+V, I+VI, I+VII, I+VIII, I+IX, I+X, II+III, II+IV, II+V, II+VI, II+VII, II+VIII, II+IX, II+X, XIV+III, XIV+IV, XIV+V, XIV+VI, XIV+VII, XIV+VIII, XIV+IX, XIV+X, XV+III, XV+IV, XV+V, XV+VI, XV+VII, XV+VIII, XV+IX and XV+X each at rates of 0.5+1.5, 1.5+0.5 and 1+1 kg/ha.

After 12 to 16 days it was ascertained that the compositions had a better herbicidal action than their components, combined with the same crop plant compatibility.

The results are given below:

| Active ingredient | I | | | | II | | | | III | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |

-continued

| Active ingredient | I | | | | II | | | | III | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 10 | 35 | 50 | 80 | 40 | 80 | 90 | 95 | 11 | 13 | 15 | 22 |
| Galium aparine | 12 | 40 | 60 | 70 | 15 | 37 | 58 | 70 | 5 | 15 | 35 | 60 |
| Matricaria chamomilla | 15 | 42 | 54 | 65 | 14 | 40 | 50 | 60 | 35 | 45 | 50 | 60 |

0 = no damage
100 = complete destruction

| Active ingredient | IV | | | | V | | | | VI | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 10 | 20 | 0 | 0 | 0 | 0 | 0 | 0 | 5 | 25 |
| Unwanted plants: | | | | | | | | | | | | |
| Avena fatua | 5 | 20 | 25 | 30 | 5 | 10 | 40 | 50 | 15 | 35 | 45 | 75 |
| Galium aparine | 15 | 30 | 50 | 70 | 0 | 6 | 10 | 20 | 10 | 30 | 45 | 61 |
| Matricaria chamomilla | 20 | 35 | 60 | 80 | 0 | 2 | 5 | 8 | 24 | 40 | 60 | 90 |

0 = no damage
100 = complete destruction

| Active ingredient | VII | | | | VIII | | | | IX | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 0 | 7 | 0 | 0 | 0 | 0 | 0 | 0 | 0 | 0 |
| Unwanted plants: | | | | | | | | | | | | |
| Avena fatua | 35 | 65 | 80 | 90 | 25 | 45 | 60 | 70 | 30 | 70 | 77 | 90 |
| Galium aparine | 0 | 6 | 10 | 13 | 0 | 10 | 14 | 18 | 0 | 5 | 8 | 10 |
| Matricaria chamomilla | 0 | 5 | 10 | 14 | 0 | 5 | 15 | 25 | 6 | 10 | 17 | 24 |

0 = no damage
100 = complete destruction

| Active ingredient | X | | | | XIV | | | | XV | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 30 | 45 | 60 | 75 | 36 | 80 | 90 | 92 | 15 | 30 | 50 | 80 |
| Galium aparine | 0 | 0 | 0 | 0 | 10 | 35 | 55 | 68 | 10 | 35 | 48 | 60 |
| Matricaria chamomilla | 0 | 2 | 10 | 15 | 11 | 37 | 54 | 70 | 20 | 50 | 68 | 85 |

0 = no damage
100 = complete destruction

| Active ingredient | I+III | | | I+IV | | | I+V | | | I+VI | | |
|---|---|---|---|---|---|---|---|---|---|---|---|---|
| kg/ha | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 |
| Crop plants: | | | | | | | | | | | | |
| Beta vulgaris | 0 | 0 | 0 | 10 | 0 | 0 | 0 | 0 | 0 | 5 | 0 | 0 |
| Unwanted plants: | | | | | | | | | | | | |
| Avena fatua | 70 | 98 | 90 | 80 | 93 | 92 | 95 | 90 | 85 | 92 | 97 | 100 |
| Galium aparine | 85 | 100 | 92 | 100 | 100 | 100 | 60 | 96 | 80 | 95 | 100 | 96 |
| Matricaria chamomilla | 100 | 100 | 100 | 100 | 100 | 100 | 63 | 90 | 80 | 100 | 100 | 100 |

0 = no damage
100 = complete destruction

| Active ingredient | I+VII | | | I+VIII | | | I+IX | | | I+X | | |
|---|---|---|---|---|---|---|---|---|---|---|---|---|
| kg/ha | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 |
| Crop plants: | | | | | | | | | | | | |
| Beta vulgaris | 0 | 0 | 0 | 0 | 0 | 0 | 0 | 0 | 0 | 0 | 0 | 0 |

-continued

| Active ingredient | I+VII | | | I+VIII | | | I+IX | | | I+X | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Unwanted plants: | | | | | | | | | | | | |
| Avena fatua | 100 | 100 | 100 | 98 | 100 | 100 | 100 | 98 | 100 | 97 | 100 | 100 |
| Galium aparine | 60 | 97 | 82 | 65 | 98 | 87 | 60 | 94 | 86 | 56 | 95 | 60 |
| Matricaria chamomilla | 66 | 90 | 84 | 68 | 90 | 85 | 70 | 92 | 82 | 64 | 90 | 80 |

0 = no damage
100 = complete destruction

| Active ingredient | II+III | | | II+IV | | | II+V | | | II+VI | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Crop plants: | | | | | | | | | | | | |
| Beta vulgaris | 0 | 0 | 0 | 10 | 0 | 0 | 0 | 0 | 0 | 5 | 0 | 0 |
| Unwanted plants: | | | | | | | | | | | | |
| Avena fatua | 90 | 100 | 100 | 77 | 90 | 93 | 100 | 100 | 100 | 90 | 95 | 100 |
| Galium aparine | 87 | 96 | 90 | 95 | 100 | 100 | 67 | 95 | 80 | 95 | 98 | 90 |
| Matricaria chamomilla | 95 | 100 | 100 | 98 | 100 | 100 | 60 | 87 | 80 | 98 | 100 | 100 |

0 = no damage
100 = complete destruction

| Active ingredient | II+VII | | | II+VIII | | | II+IX | | | II+X | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 69 | 95 | 80 | 70 | 97 | 85 | 65 | 95 | 80 | 60 | 92 | 75 |
| Matricaria chamomilla | 65 | 85 | 80 | 68 | 88 | 82 | 70 | 90 | 86 | 65 | 85 | 80 |

0 = no damage
100 = complete destruction

| Active ingredient | XIV+III | | | XIV+IV | | | XIV+V | | | XIV+VI | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Crop plants: | | | | | | | | | | | | |
| Beta vulgaris | 0 | 0 | 0 | 10 | 0 | 0 | 0 | 0 | 0 | 5 | 0 | 0 |
| Unwanted plants: | | | | | | | | | | | | |
| Avena fatua | 90 | 100 | 100 | 96 | 100 | 100 | 100 | 100 | 100 | 100 | 100 | 100 |
| Galium aparine | 80 | 96 | 90 | 95 | 100 | 97 | 64 | 90 | 80 | 97 | 100 | 90 |
| Matricaria chamomilla | 95 | 100 | 100 | 100 | 100 | 95 | 60 | 90 | 80 | 98 | 100 | 100 |

0 = no damage
100 = complete destruction

| Active ingredient | XIV+VII | | | XIV+VIII | | | XIV+IX | | | XIV+X | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 65 | 92 | 80 | 68 | 90 | 83 | 63 | 92 | 80 | 55 | 95 | 76 |
| Matricaria chamomilla | 65 | 90 | 81 | 70 | 90 | 80 | 70 | 96 | 85 | 64 | 92 | 79 |

0 = no damage
100 = complete destruction

| Active ingredient | XV+III | | | XV+IV | | | XV+V | | | XV+VI | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Crop plants: | | | | | | | | | | | | |
| Beta vulgaris | 0 | 0 | 0 | 10 | 0 | 0 | 0 | 0 | 0 | 5 | 0 | 0 |
| Unwanted plants: | | | | | | | | | | | | |
| Avena fatua | 76 | 94 | 80 | 85 | 90 | 87 | 92 | 90 | 84 | 97 | 98 | 95 |
| Galium aparine | 82 | 90 | 87 | 96 | 95 | 98 | 64 | 85 | 78 | 92 | 95 | 92 |
| Matricaria chamomilla | 100 | 100 | 100 | 100 | 100 | 100 | 70 | 100 | 90 | 100 | 100 | 100 |

0 = no damage
100 = complete destruction

| Active ingredient | XV+VII | | | XV+VIII | | | XV+IX | | | XV+X | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 98 | 100 | 100 | 100 | 100 | 100 | 98 | 100 | 100 |
| Galium aparine | 65 | 85 | 80 | 62 | 90 | 80 | 60 | 87 | 76 | 54 | 85 | 77 |
| Matricaria chamomilla | 75 | 90 | 90 | 80 | 100 | 90 | 80 | 100 | 94 | 75 | 99 | 88 |

0 = no damage
100 = complete destruction

EXAMPLE 4

In the open, various plants were treated at a growth height of from 2 to 18 cm with the following amounts of the following individual active ingredients and compositions thereof as oil dispersions:

I. 2.3-dihydro-3,3-dimethyl-2-ethoxybenzofuran-5-ylmethylamino sulfonate

II. 2,3-dihydro-3,3-dimethyl-2-ethoxybenzofuran-5-yldimethylamino sulfonate

III. 1-phenyl-4-amino-5-chloropyridazone-(6)

IV. 3-methoxycarbonylaminophenyl-N-(3'-methylphenyl)carbamate

V. ethyl N-ethyl-N-cyclohexylthiol carbamate

VI. 3-cyclohexyl-5,6-trimethylene uracil

VII. 1,2-dimethyl-3,5-diphenylpyrazolium methyl sulfate

VIII. ethyl-N-benzoyl-N-(3,4-dichlorophenyl)-2-aminopropionate

IX. 4-chlorobutyn-2-yl-1 N-3-chlorophenylcarbamate

X. methyl α-chloro-β-(4-chlorophenyl)-propionate

XIV. 2,3-dihydro-3,3-dimethyl-2-methoxybenzofuran-5-yldimethylamino sulfonate

XV. 2,3-dihydro-3,3-dimethyl-2-methoxybenzofuran-5-ylmethylamino sulfonate each at rates of 1, 1.5, 2, 3 and 4 kg/ha I+III, I+IV, I+V, I+VI, I+VII, I+VIII, I+IX, I+X, II+III, II+IV, II+V, II+VI, II+VII, II+VIII, II+IX, II+X, XIV+III, XIV+IV, XIV+V, XIV+VI, XIV+VII, XIV+VIII, XIV+IX, XIV+X, XV+III, XV+IV, XV+V, XV+VI, XV+VII, XV+VIII, XV+IX and XV+X each at rates of 1+2, 2+1, 1.5+1.5, 2+2, 3+1 and 1+3 kg/ha and, for comparison, XI. 2-chloro-4,6-diethylamino-1,3,5-triazine at a rate of 3 kg/ha II+XI at a rate of 1+3 kg/ha.

After 12 to 15 days it was ascertained that the compositions had better crop plant compatibility than active ingredient XI in the composition II+XI, combined with the same herbicidal action. The results are given below:

| Active ingredient | I | | | | | II | | | | |
|---|---|---|---|---|---|---|---|---|---|---|
| kg/ha | 1 | 1.5 | 2 | 3 | 4 | 1 | 1.5 | 2 | 3 | 4 |
| Crop plants: | | | | | | | | | | |
| Beta vulgaris | 0 | 0 | 0 | 0 | 5 | 0 | 0 | 0 | 5 | 8 |
| Unwanted plants: | | | | | | | | | | |
| Avena fatua | 35 | 50 | 80 | 90 | 97 | 80 | 90 | 95 | 98 | 100 |
| Galium aparine | 40 | 60 | 70 | 80 | 90 | 37 | 58 | 70 | 80 | 92 |
| Matricaria chamomilla | 42 | 54 | 65 | 76 | 87 | 40 | 50 | 60 | 70 | 85 |

0 = no damage
100 = complete destruction

| Active ingredient | III | | | | | IV | | | | |
|---|---|---|---|---|---|---|---|---|---|---|
| kg/ha | 1 | 1.5 | 2 | 3 | 4 | 1 | 1.5 | 2 | 3 | 4 |
| Crop plants: | | | | | | | | | | |
| Beta vulgaris | 0 | 0 | 0 | 0 | 10 | 0 | 10 | 20 | 30 | 45 |
| Unwanted plants: | | | | | | | | | | |
| Avena fatua | 13 | 15 | 22 | 40 | 65 | 20 | 25 | 30 | 40 | 50 |
| Galium aparine | 15 | 35 | 70 | 80 | 90 | 30 | 50 | 70 | 80 | 90 |

-continued

| Active ingredient | III | | | | | IV | | | | |
|---|---|---|---|---|---|---|---|---|---|---|
| kg/ha | 1 | 1.5 | 2 | 3 | 4 | 1 | 1.5 | 2 | 3 | 4 |
| *Matricaria chamomilla* | 45 | 50 | 60 | 90 | 100 | 35 | 60 | 80 | 95 | 100 |

0 = no damage
100 = complete destruction

| Active ingredient | V | | | | | VI | | | | |
|---|---|---|---|---|---|---|---|---|---|---|
| kg/ha | 1 | 1.5 | 2 | 3 | 4 | 1 | 1.5 | 2 | 3 | 4 |
| Crop plants: | | | | | | | | | | |
| *Beta vulgaris* | 0 | 0 | 0 | 0 | 10 | 0 | 5 | 25 | 30 | 50 |
| Unwanted plants: | | | | | | | | | | |
| *Avena fatua* | 10 | 40 | 50 | 70 | 87 | 35 | 45 | 75 | 85 | 96 |
| *Galium aparine* | 6 | 10 | 20 | 38 | 50 | 30 | 45 | 61 | 74 | 80 |
| *Matricaria chamomilla* | 2 | 5 | 8 | 15 | 40 | 40 | 60 | 90 | 95 | 100 |

0 = no damage
100 = complete destruction

| Active ingredient | VII | | | | | VIII | | | | |
|---|---|---|---|---|---|---|---|---|---|---|
| kg/ha | 1 | 1.5 | 2 | 3 | 4 | 1 | 1.5 | 2 | 3 | 4 |
| Crop plants: | | | | | | | | | | |
| *Beta vulgaris* | 0 | 3 | 7 | 10 | 15 | 0 | 0 | 0 | 5 | 8 |
| Unwanted plants: | | | | | | | | | | |
| *Avena fatua* | 65 | 80 | 90 | 95 | 100 | 45 | 60 | 70 | 95 | 100 |
| *Galium aparine* | 6 | 10 | 13 | 26 | 35 | 10 | 14 | 18 | 35 | 45 |
| *Matricaria chamomilla* | 5 | 10 | 14 | 20 | 30 | 5 | 15 | 25 | 30 | 40 |

0 = no damage
100 = complete destruction

| Active ingredient | IX | | | | | X | | | | |
|---|---|---|---|---|---|---|---|---|---|---|
| kg/ha | 1 | 1.5 | 2 | 3 | 4 | 1 | 1.5 | 2 | 3 | 4 |
| Crop plants: | | | | | | | | | | |
| *Beta vulgaris* | 0 | 0 | 0 | 10 | 18 | 0 | 0 | 0 | 0 | 0 |
| Unwanted plants: | | | | | | | | | | |
| *Avena fatua* | 70 | 77 | 90 | 100 | 100 | 45 | 60 | 75 | 85 | 100 |
| *Galium aparine* | 5 | 8 | 10 | 16 | 25 | 0 | 0 | 0 | 10 | 20 |
| *Matricaria chemomilla* | 10 | 17 | 24 | 29 | 34 | 2 | 10 | 15 | 20 | 25 |

0 = no damage
100 = complete destruction

| Active ingredient | XIV | | | | | XV | | | | | XI | |
|---|---|---|---|---|---|---|---|---|---|---|---|---|
| kg/ha | 1 | 1.5 | 2 | 3 | 4 | 1 | 1.5 | 2 | 3 | 4 | 3 | 4 |
| Crop plants: | | | | | | | | | | | | |
| *Beta vulgaris* | 0 | 0 | 0 | 3 | 7 | 0 | 0 | 0 | 0 | 0 | 100 | 100 |
| Unwanted plants: | | | | | | | | | | | | |
| *Avena fatua* | 80 | 90 | 92 | 97 | 100 | 30 | 50 | 80 | 90 | 95 | 90 | 100 |
| *Galium aparine* | 35 | 55 | 68 | 78 | 90 | 35 | 48 | 60 | 75 | 86 | 70 | 100 |
| *Matricaria chamomilla* | 37 | 54 | 70 | 75 | 82 | 50 | 68 | 85 | 92 | 97 | 100 | 100 |

0 = no damage
100 = complete destruction

| Active ingredient | I+III | | | | | | I+IV | | | | | |
|---|---|---|---|---|---|---|---|---|---|---|---|---|
| kg/ha | 1 / 2 | 2 / 1 | 1.5 / 1.5 | 2 / 2 | 3 / 1 | 1 / 3 | 1 / 2 | 2 / 1 | 1.5 / 1.5 | 2 / 2 | 3 / 1 | 1 / 3 |
| Crop plants: | | | | | | | | | | | | |
| *Beta vulgaris* | 0 | 0 | 0 | 0 | 0 | 0 | 20 | 0 | 10 | 20 | 0 | 30 |
| Unwanted plants: | | | | | | | | | | | | |
| *Avena fatua* | 97 | 100 | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 | 100 | 100 |

-continued

| Active ingredient | I+III | | | | | | I+IV | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| *Matricaria chamomilla* | 100 | 100 | 100 | 100 | 100 | 100 | 100 | 100 | 100 | 100 | 100 | 100 |

0 = no damage
100 = complete destruction

| Active ingredient | I+V | | | | | | I+VI | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| *Beta vulgaris* | 0 | 0 | 0 | 0 | 0 | 0 | 10 | 0 | 5 | 10 | 0 | 30 |
| Unwanted plants: | | | | | | | | | | | | |
| *Avena fatua* | 100 | 100 | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 | 100 | 100 |
| *Matricaria chamomilla* | 87 | 100 | 100 | 100 | 100 | 98 | 100 | 100 | 100 | 100 | 100 | 100 |

0 = no damage
100 = complete destruction

| Active ingredient | I+VII | | | | | | I+VIII | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| *Beta vulgaris* | 7 | 0 | 3 | 7 | 0 | 10 | 0 | 0 | 0 | 0 | 0 | 5 |
| Unwanted plants: | | | | | | | | | | | | |
| *Avena fatua* | 100 | 100 | 100 | 100 | 100 | 100 | 100 | 100 | 100 | 100 | 100 | 100 |
| *Galium aparine* | 90 | 100 | 100 | 100 | 100 | 100 | 100 | 100 | 100 | 100 | 100 | 100 |
| *Matricaria chamomilla* | 96 | 100 | 100 | 100 | 100 | 100 | 100 | 100 | 100 | 100 | 100 | 100 |

0 = no damage
100 = complete destruction

| Active ingredient | I+IX | | | | | | I+X | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| *Beta vulgaris* | 0 | 0 | 0 | 0 | 0 | 10 | 0 | 0 | 0 | 0 | 0 | 0 |
| Unwanted plants: | | | | | | | | | | | | |
| *Avena fatua* | 100 | 100 | 100 | 100 | 100 | 96 | 82 | 100 | 100 | 100 | 100 | 88 |
| *Galium aparine* | 88 | 100 | 100 | 100 | 100 | 100 | 97 | 100 | 100 | 100 | 100 | 100 |
| *Matricaria chamomilla* | 100 | 100 | 100 | 100 | 100 | 100 | 100 | 100 | 100 | 100 | 100 | 100 |

0 = no damage
100 = complete destruction

| Active ingredient | II+III | | | | | | II+IV | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| *Beta vulgaris* | 0 | 0 | 0 | 0 | 5 | 0 | 20 | 0 | 10 | 20 | 5 | 0 |
| Unwanted plants: | | | | | | | | | | | | |
| *Avena fatua* | 100 | 100 | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 | 100 | 100 |
| *Matricaria chamomilla* | 100 | 100 | 100 | 100 | 100 | 100 | 100 | 100 | 100 | 100 | 100 | 100 |

0 = no damage
100 = complete destruction

| Active ingredient | II+V | | | | | | II+VI | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| *Beta vulgaris* | 0 | 0 | 0 | 0 | 5 | 0 | 10 | 0 | 5 | 10 | 5 | 30 |

-continued

| Active ingredient | II+V | | | | | | II+VI | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 97 | 100 | 100 | 100 | 100 | 100 | 100 | 100 | 100 | 100 | 100 | 100 |
| Matricaria chamomilla | 85 | 100 | 93 | 100 | 100 | 94 | 100 | 100 | 100 | 100 | 100 | 100 |

0 = no damage
100 = complete destruction

| Active ingredient | II+VII | | | | | | II+VIII | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| Beta vulgaris | 7 | 0 | 3 | 7 | 5 | 10 | 0 | 0 | 0 | 0 | 5 | 5 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 90 | 100 | 100 | 100 | 100 | 100 | 95 | 100 | 100 | 100 | 100 | 100 |
| Matricaria chamomilla | 94 | 100 | 100 | 100 | 100 | 100 | 100 | 100 | 100 | 100 | 100 | 100 |

0 = no damage
100 = complete destruction

| Active ingredient | II+IX | | | | | | II+X | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| Beta vularis | 0 | 0 | 0 | 0 | 0 | 10 | 0 | 0 | 0 | 0 | 5 | 0 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 87 | 100 | 100 | 100 | 100 | 93 | 80 | 100 | 100 | 100 | 100 | 87 |
| Matricaria chamomilla | 100 | 100 | 100 | 100 | 100 | 100 | 91 | 100 | 100 | 100 | 100 | 100 |

0 = no damage
100 = complete destruction

| Active ingredient | XIV+III | | | | | | XIV+IV | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| Beta vulgaris | 0 | 0 | 0 | 0 | 3 | 0 | 20 | 0 | 10 | 20 | 3 | 30 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 100 | 100 | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 | 100 | 100 |

0 = no damage
100 = complete destruction

| Active ingredient | XIV+V | | | | | | XIV+VI | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants: | | | | | | | | | | | | |
| Beta vulgaris | 0 | 0 | 0 | 0 | 3 | 0 | 10 | 0 | 5 | 10 | 3 | 30 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 95 | 100 | 100 | 100 | 100 | 100 | 100 | 100 | 100 | 100 | 100 | 100 |
| Matricaria chamomilla | 85 | 100 | 100 | 100 | 100 | 89 | 100 | 100 | 100 | 100 | 100 | 100 |

0 = no damage
100 = complete destruction

| Active ingredient | XIV+VII | | | | | | XIV+VIII | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants:<br>Beta vulgaris | 7 | 0 | 3 | 7 | 3 | 10 | 0 | 0 | 0 | 0 | 0 | 5 |
| Unwanted plants:<br>Avena fatua | 100 | 100 | 100 | 100 | 100 | 100 | 100 | 100 | 100 | 100 | 100 | 100 |
| Galium aparine | 88 | 100 | 100 | 100 | 100 | 100 | 93 | 100 | 100 | 100 | 100 | 100 |
| Matricaria chamomilla | 91 | 100 | 100 | 100 | 100 | 96 | 100 | 100 | 100 | 100 | 100 | 100 |

0 = no damage
100 = complete destruction

| Active ingredient | XIV+IX | | | | | | XIV+X | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants:<br>Beta vulgaris | 0 | 0 | 0 | 0 | 3 | 10 | 0 | 0 | 0 | 0 | 3 | 0 |
| Unwanted plants:<br>Avena fatua | 100 | 100 | 100 | 100 | 100 | 100 | 100 | 100 | 100 | 100 | 100 | 100 |
| Galium aparine | 85 | 100 | 100 | 100 | 100 | 91 | 78 | 100 | 93 | 100 | 100 | 85 |
| Matricaria chamomilla | 100 | 100 | 100 | 100 | 100 | 100 | 89 | 100 | 100 | 100 | 100 | 97 |

0 = no damage
100 = complete destruction

| Active ingredient | XV+III | | | | | | XV+IV | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants:<br>Beta vulgaris | 0 | 0 | 0 | 0 | 0 | 0 | 20 | 0 | 10 | 20 | 0 | 30 |
| Unwanted plants:<br>Avena fatua | 92 | 100 | 100 | 100 | 100 | 100 | 100 | 100 | 100 | 100 | 100 | 100 |
| Galium aparine | 100 | 100 | 100 | 100 | 100 | 100 | 100 | 100 | 100 | 100 | 100 | 100 |
| Matricaria chamomilla | 100 | 100 | 100 | 100 | 100 | 100 | 100 | 100 | 100 | 100 | 100 | 100 |

0 = no damage
100 = complete destruction

| Active ingredient | XV+V | | | | | | XV+VI | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants:<br>Beta vulgaris | 0 | 0 | 0 | 0 | 0 | 0 | 10 | 0 | 5 | 10 | 0 | 30 |
| Unwanted plants:<br>Avena fatua | 100 | 100 | 100 | 100 | 100 | 100 | 100 | 100 | 100 | 100 | 100 | 100 |
| Galium aparine | 95 | 100 | 97 | 100 | 100 | 100 | 100 | 100 | 100 | 100 | 100 | 100 |
| Matricaria chamomilla | 98 | 100 | 100 | 100 | 100 | 100 | 100 | 100 | 100 | 100 | 100 | 100 |

0 = no damage
100 = complete destruction

| Active ingredient | XV+VII | | | | | | XV+VIII | | | | | |
|---|---|---|---|---|---|---|---|---|---|---|---|---|
| kg/ha | 1<br>2 | 2<br>1 | 1.5<br>1.5 | 2<br>2 | 3<br>1 | 1<br>3 | 1<br>2 | 2<br>1 | 1.5<br>1.5 | 2<br>2 | 3<br>1 | 1<br>3 |
| Crop plants:<br>Beta vulgaris | 7 | 0 | 3 | 7 | 0 | 10 | 0 | 0 | 0 | 0 | 0 | 5 |
| Unwanted plants:<br>Avena fatua | 100 | 100 | 100 | 100 | 30 | 100 | 100 | 100 | 100 | 100 | 100 | 100 |
| Galium aparine | 88 | 100 | 97 | 100 | 30 | 100 | 93 | 100 | 100 | 100 | 100 | 100 |
| Matricaria chamomilla | 100 | 100 | 100 | 100 | 30 | 100 | 100 | 100 | 100 | 100 | 100 | 100 |

0 = no damage
100 = complete destruction

| Active ingredient | XV+IX | | | | | | XV+X | | | | | |
|---|---|---|---|---|---|---|---|---|---|---|---|---|
| kg/ha | 1 2 | 2 1 | 1.5 1.5 | 2 2 | 3 1 | 1 3 | 1 2 | 2 1 | 1.5 1.5 | 2 2 | 3 1 | 1 3 |
| Crop plants: | | | | | | | | | | | | |
| Beta vulgaris | 0 | 0 | 0 | 0 | 0 | 10 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 100 | 86 | 95 | 100 | 100 | 91 | 75 | 100 | 87 | 100 | 100 | 86 |
| Matricaria chamomilla | 100 | 100 | 100 | 100 | 100 | 100 | 100 | 100 | 100 | 100 | 100 | 100 |

0 = no damage
100 = complete destruction

| Active ingredient | XI | | II+XI |
|---|---|---|---|
| kg/ha | 3 | 4 | 1+3 |
| Crop plants: | | | |
| Beta vulgaris | 100 | 100 | 100 |
| Unwanted plants: | | | |
| Avena fatua | 90 | 100 | 100 |
| Galium aparine | 100 | 100 | 100 |
| Matricaria chamomilla | 100 | 100 | 100 |

0 = no damage
100 = complete destruction

EXAMPLE 5

In the greenhouse, various plants were treated at a growth height of from 1 to 10 cm with the following amounts of the following individual active ingredients and compositions thereof as emulsions or dispersions:

III. 1-phenyl-4-amino-5-chloropyridazone-(6)

IV. 3-methoxycarbonylaminophenyl-N-(3'-methylphenyl)carbamate

VI. 3-cyclohexyl-5,6-trimethylene uracil

VII. 1,2-dimethyl-3,5-diphenylpyrazolium methyl sulfate

VIII. 1-ethyl-N-benzoyl-N-(3,4-dichlorophenyl)-2-aminopropionate

IX. 4-chlorobutyn-2-yl-1 N-3-chlorophenylcarbamate

X. methyl α-chloro-β-(4-chlorophenyl)-propionate

XVI. 2,3-dihydro-3,3-dimethyl-2-propoxybenzofuran-5-yldimethylamino sulfonate

XVII. 2,3-dihydro-3,3-dimethyl-2-isopropoxybenzofuran-5-yldimethylamino sulfonate XVIII. 2,3-dihydro-3,3-dimethyl-2-allyloxybenzofuran-5-ylmethylamino sulfonate XIX. 2,3-dihydro-3,3-dimethyl-2-propargyloxybenzofuran-5-ylmethylamino sulfonate each at rates of 0.5, 1, 1.5 and 2 kg/ha III+XVI, III+XVII, III+XVIII, III+XIX, IV+XVI, IV+XVII, IV+XVIII, IV+XIX, VI+XVI, VI+XVII, VI+XVIII, VI+XIX, VII+XVI, VIII+XVII, IX+XVIII and X+XIX each at rates of 0.5+1.5, 1.5+0.5 and 1+1 kg/ha III+X-VI+VI, III+XVII+IX, III+XVIII+IV, III+XVIII+VII, III+XIX+VIII, III+XIX+X, XVI+IV+VI, XVII+IV+X, XVIII+IV+IX, XIX+IV+VII and XVIII+IV+VIII each at rates of 0.5°1+0.5, 1+0.5+0.5 and 0.5+0.5+1 kg/ha.

After 12 to 15 days it was ascertained that the compositions had a better herbicidal action than their components, combined with the same crop plant compatibility.

The results are given below:

| Active ingredient | III | | | | IV | | | | VI | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 0 | 0 | 0 | 0 | 10 | 20 | 0 | 0 | 5 | 25 |
| Unwanted plants: | | | | | | | | | | | | |
| Avena fatua | 11 | 13 | 15 | 22 | 5 | 20 | 25 | 30 | 15 | 35 | 45 | 75 |
| Galium aparine | 5 | 15 | 35 | 60 | 15 | 30 | 50 | 70 | 10 | 30 | 45 | 61 |
| Matricaria chamomilla | 35 | 45 | 50 | 60 | 20 | 35 | 60 | 80 | 24 | 40 | 60 | 90 |

0 = no damage
100 = complete destruction

| Active ingredient | VII | | | | VIII | | | | IX | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 0 | 7 | 0 | 0 | 0 | 0 | 0 | 0 | 0 | 0 |
| Unwanted plants: | | | | | | | | | | | | |
| Avena fatua | 35 | 65 | 80 | 90 | 25 | 45 | 60 | 70 | 30 | 70 | 77 | 90 |
| Galium aparine | 0 | 6 | 10 | 13 | 0 | 10 | 14 | 18 | 0 | 5 | 8 | 10 |
| Matricaria chamomilla | 0 | 5 | 10 | 14 | 0 | 5 | 15 | 25 | 6 | 10 | 17 | 24 |

0 = no damage
100 = complete destruction

| Active ingredient | X | | | | XIV | | | | XVII | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 30 | 45 | 60 | 75 | 25 | 40 | 50 | 70 | 20 | 45 | 50 | 75 |
| Galium aparine | 0 | 0 | 0 | 0 | 15 | 30 | 45 | 60 | 20 | 35 | 50 | 65 |
| Matricaria chamomilla | 0 | 2 | 10 | 15 | 12 | 36 | 48 | 60 | 15 | 35 | 45 | 60 |

0 = no damage
100 = complete destruction

| Active ingredient | XVIII | | | | XIX | | | | III+XVI | | |
|---|---|---|---|---|---|---|---|---|---|---|---|
| kg/ha | 0.5 | 1 | 1.5 | 2 | 0.5 | 1 | 1.5 | 2 | 0.5 / 1.5 | 1.5 / 0.5 | 1 / 1 |
| Crop plants: | | | | | | | | | | | |
| Beta vulgaris | 0 | 0 | 0 | 0 | 0 | 0 | 0 | 0 | 0 | 0 | 0 |
| Unwanted plants: | | | | | | | | | | | |
| Avena fatua | 20 | 35 | 45 | 50 | 15 | 30 | 40 | 60 | 98 | 80 | 90 |
| Galium aparine | 20 | 40 | 60 | 75 | 10 | 30 | 50 | 60 | 90 | 90 | 84 |
| Matricaria chamomilla | 20 | 40 | 50 | 65 | 13 | 30 | 40 | 55 | 100 | 95 | 100 |

0 = no damage
100 = complete destruction

| Active ingredient | III+XVII | | | III+XVIII | | | III+XIX | | | IV+XVI | | |
|---|---|---|---|---|---|---|---|---|---|---|---|---|
| kg/ha | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 |
| Crop plants: | | | | | | | | | | | | |
| Beta vulgaris | 0 | 0 | 0 | 0 | 0 | 0 | 0 | 0 | 0 | 0 | 10 | 0 |
| Unwanted plants: | | | | | | | | | | | | |
| Avena fatua | 95 | 75 | 100 | 100 | 70 | 85 | 90 | 70 | 80 | 90 | 87 | 100 |
| Galium aparine | 97 | 92 | 90 | 98 | 90 | 95 | 92 | 82 | 82 | 95 | 100 | 98 |
| Matricaria chamomilla | 100 | 98 | 100 | 100 | 100 | 100 | 100 | 95 | 100 | 100 | 100 | 100 |

0 = no damage
100 = complete destruction

| Active ingredient | IV+XVII | | | IV+XVIII | | | IV+XIX | | | VI+XVI | | |
|---|---|---|---|---|---|---|---|---|---|---|---|---|
| kg/ha | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 |
| Crop plants: | | | | | | | | | | | | |
| Beta vulgaris | 0 | 10 | 0 | 0 | 10 | 0 | 0 | 10 | 0 | 0 | 5 | 0 |
| Unwanted plants: | | | | | | | | | | | | |
| Avena fatua | 90 | 80 | 100 | 90 | 80 | 97 | 80 | 80 | 88 | 92 | 100 | 100 |
| Galium aparine | 97 | 100 | 100 | 100 | 100 | 100 | 96 | 97 | 96 | 96 | 96 | 95 |
| Matricaria chamomilla | 95 | 100 | 100 | 100 | 100 | 100 | 95 | 100 | 95 | 100 | 100 | 100 |

0 = no damage
100 = complete destruction

| Active ingredient | VI+XVII | | | VI+XVIII | | | VI+XIX | | | VII+XVI | | |
|---|---|---|---|---|---|---|---|---|---|---|---|---|
| kg/ha | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 |
| Crop plants: | | | | | | | | | | | | |
| Beta vulgaris | 0 | 5 | 0 | 0 | 5 | 0 | 0 | 5 | 0 | 0 | 0 | 0 |
| Unwanted plants: | | | | | | | | | | | | |
| Avena fatua | 97 | 98 | 100 | 95 | 97 | 100 | 92 | 98 | 96 | 100 | 100 | 100 |
| Galium aparine | 95 | 96 | 98 | 100 | 96 | 100 | 98 | 92 | 95 | 80 | 62 | 75 |
| Matricaria chamomilla | 100 | 100 | 100 | 100 | 100 | 100 | 100 | 100 | 100 | 90 | 60 | 80 |

0 = no damage
100 = complete destruction

| Active ingredient | VIII+XVIII | | | IX+XVIII | | | X+XIX | | | III+XVI+VI | | |
|---|---|---|---|---|---|---|---|---|---|---|---|---|
| kg/ha | 0.5<br>1.5 | 1.5<br>0.5 | 1<br>1 | 0.5<br>1.5 | 1.5<br>0.5 | 1<br>1 | 0.5<br>1.5 | 1.5<br>0.5 | 1<br>1 | 0.5<br>1<br>0.5 | 1<br>0.5<br>0.5 | 0.5<br>0.5<br>1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 95 | 100 |
| Galium aparine | 88 | 70 | 80 | 95 | 72 | 96 | 90 | 58 | 72 | 82 | 80 | 87 |
| Matricaria chamomilla | 82 | 70 | 80 | 92 | 75 | 92 | 77 | 60 | 75 | 100 | 100 | 100 |

0 = no damage
100 = complete destruction

| Active ingredient | III+XVII+IX | | | III+XVIII+IV | | | III+XVIII+VII | | | III+XIX+VIII | | |
|---|---|---|---|---|---|---|---|---|---|---|---|---|
| kg/ha | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 90 | 75 | 90 | 100 | 100 | 100 | 100 | 95 | 100 |
| Galium aparine | 80 | 73 | 70 | 95 | 88 | 97 | 82 | 70 | 73 | 75 | 68 | 65 |
| Matricaria chamomilla | 100 | 100 | 97 | 100 | 100 | 100 | 100 | 100 | 98 | 100 | 100 | 90 |

0 = no damage
100 = complete destruction

| Active ingredient | III+XIX+X | | | XVI+IV+VI | | | XVII+IV+X | | | XVIII+IV+IX | | |
|---|---|---|---|---|---|---|---|---|---|---|---|---|
| kg/ha | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 95 | 100 | 100 | 100 | 100 | 100 | 100 | 100 | 100 | 100 | 100 |
| Galium aparine | 72 | 80 | 60 | 90 | 92 | 100 | 87 | 90 | 75 | 92 | 90 | 80 |
| Matricaria chamomilla | 100 | 100 | 90 | 100 | 100 | 100 | 95 | 90 | 80 | 96 | 97 | 90 |

0 = no damage
100 = complete destruction

| Active ingredient | XIX+IV+VII | | | XVIII+IV+VIII | | |
|---|---|---|---|---|---|---|
| kg/ha | 0.5<br>1<br>0.5 | 1<br>0.5<br>0.5 | 0.5<br>0.5<br>1 | 0.5<br>1<br>0.5 | 1<br>0.5<br>0.5 | 0.5<br>0.5<br>1 |
| Crop plants: | | | | | | |
| Beta vulgaris | 0 | 0 | 0 | 0 | 0 | 0 |
| Unwanted plants: | | | | | | |
| Avena fatua | 100 | 100 | 100 | 100 | 100 | 100 |
| Galium aparine | 77 | 80 | 74 | 97 | 90 | 87 |
| Matricaria chamomilla | 93 | 96 | 80 | 98 | 96 | 89 |

0 = no damage
100 = complete destruction

EXAMPLE 6

In the greenhouse, loamy sandy soil was filled into pots and sown with various seeds. The soil prepared in this manner ws then treated with the following amounts of the following individual active ingredients and compositions thereof as emulsions or dispersions:

III. 1-phenyl-4-amino-5-chloropyridazone-(6)
V. ethyl N-ethyl-N-cyclogexylthiol carbamate
VI. 3-cyclohexyl-5,6-trimethylene uracil
XII. 2,3-dichloroallyl N,N-diisopropylthiol carbamate
XIII. 2,3,3-trichloroallyl N,N-diisopropylthiol carbamate
XVI. 2,3-dihydro-3,3-dimethyl-2-propoxybenzofuran-5-yldimethylamino sulfonate
XVII. 2,3-dihydro-3,3-dimethyl-2-isopropoxybenzofuran-5-yldimethylamino sulfonate
XVIII. 2,3-dihydro-3,3-dimethyl-2-allyloxybenzofuran-5-ylmethylamino sulfonate
XIX. 2,3-dihydro-3,3-dimethyl-2-propargyloxybenzofuran-5-ylmethylamino sulfonate
XX. 2,3-dihydro-3,3-dimethyl-2-allyloxybenzofuran-5-yldimethylamino sulfonate III, V, XII and XIII each at rates of 0.5, 1, 1.5 and 2 kg/ha VI, XVI, XVII, XVIII, XIX and XX each at rates of 0.5, 0.75, 1, 1.5 and 2 kg/ha III+XVI, III+XVII, III+XVIII, III+XIX, III+XX, XVI+V, XVII+XII, XVIII+XII, XIX+XIII and XX+XIII each at rates of 0.5+1.5, 1.5+0.5 and 1+1 kg/ha III+X-VII+XII, III+XVI+V, III+XVIII+XIII, III+XIX+VI, III+XX+XII, XVI+XII+VI, XVII+XIII+V, XVIII+λ VI+V and XX+XII+V each at rates of 0.5+0.5+1, 1+0.5+0.5 and 0.5+1+0.5 kg/ha VI+XVI+XVII, VI+XVIII VI+XIX and VI+XX each at rates of 0.5+1, 1+0.5 and 0.75+0.75 kg/ha.

After 3 to 4 weeks it was ascertained that the compositions had a better herbicidal action than their components, combined with the same crop plant compatibility.

The results are given below:

| Active ingredient | III | | | | V | | | | VI | | | |
|---|---|---|---|---|---|---|---|---|---|---|---|---|
| kg/ha | 0.5 | 1 | 1.5 | 2 | 0.5 | 1 | 1.5 | 2 | 0.5 | 0.75 | 1 | 1.5 | 2 |
| Crop plants: | | | | | | | | | | | | | |
| Beta vulgaris | 0 | 0 | 0 | 0 | 0 | 0 | 0 | 0 | 0 | 0 | 0 | 0 | 20 |
| Unwanted plants: | | | | | | | | | | | | | |
| Avena fatua | 5 | 12 | 15 | 20 | 12 | 30 | 40 | 60 | 5 | 15 | 18 | 20 | 30 |
| Galium aparine | 15 | 40 | 50 | 75 | 0 | 10 | 15 | 20 | 10 | 30 | 50 | 60 | 75 |
| Matricaria chamomilla | 30 | 50 | 60 | 85 | 5 | 7 | 9 | 10 | 20 | 56 | 70 | 75 | 95 |

0 = no damage
100 = complete destruction

| Active ingredient | XII | | | | XIII | | | | XVI | | | |
|---|---|---|---|---|---|---|---|---|---|---|---|---|
| kg/ha | 0.5 | 1 | 1.5 | 2 | 0.5 | 1 | 1.5 | 2 | 0.5 | 0.75 | 1 | 1.5 | 2 |
| Crop plants: | | | | | | | | | | | | | |
| Beta vulgaris | 0 | 0 | 0 | 10 | 0 | 0 | 0 | 7 | 0 | 0 | 0 | 0 | 0 |
| Unwanted plants: | | | | | | | | | | | | | |
| Avena fatua | 20 | 60 | 83 | 95 | 30 | 67 | 90 | 98 | 20 | 30 | 40 | 70 | 90 |
| Galium aparine | 0 | 0 | 5 | 8 | 0 | 0 | 5 | 10 | 24 | 30 | 36 | 52 | 65 |
| Matricaria chamomilla | 5 | 10 | 13 | 19 | 9 | 12 | 15 | 21 | 5 | 15 | 24 | 30 | 42 |

0 = no damage
100 = complete destruction

| Active ingredient | XVII | | | | | XVIII | | | | | XIX | | | | |
|---|---|---|---|---|---|---|---|---|---|---|---|---|---|---|---|
| kg/ha | 0.5 | 0.75 | 1 | 1.5 | 2 | 0.5 | 0.75 | 1 | 1.5 | 2 | 0.5 | 0.75 | 1 | 1.5 | 2 |
| Crop plants: | | | | | | | | | | | | | | | |
| Beta vulgaris | 0 | 0 | 0 | 0 | 0 | 0 | 0 | 0 | 0 | 0 | 0 | 0 | 0 | 0 | 0 |
| Unwanted plants: | | | | | | | | | | | | | | | |
| Avena fatua | 25 | 40 | 50 | 75 | 90 | 30 | 45 | 55 | 80 | 95 | 15 | 35 | 50 | 65 | 80 |
| Galium aparine | 20 | 28 | 35 | 55 | 65 | 25 | 34 | 40 | 60 | 70 | 12 | 20 | 30 | 50 | 60 |
| Matricaria chamomilla | 8 | 17 | 26 | 35 | 45 | 10 | 20 | 30 | 40 | 50 | 6 | 15 | 25 | 32 | 40 |

0 = no damage
100 = complete destruction

| Active ingredient | XX | | | | | III+XVI | | | III+XVII | | | III+XVIII | | |
|---|---|---|---|---|---|---|---|---|---|---|---|---|---|---|
| kg/ha | 0.5 | 0.75 | 1 | 1.5 | 2 | 0.5 / 1.5 | 1.5 / 0.5 | 1 / 1 | 0.5 / 1.5 | 1.5 / 0.5 | 1 / 1 | 0.5 / 1.5 | 1.5 / 0.5 | 1 / 1 |
| Crop plants: | | | | | | | | | | | | | | |
| Beta vulgaris | 0 | 0 | 0 | 0 | 0 | 0 | 0 | 0 | 0 | 0 | 0 | 0 | 0 | 0 |
| Unwanted plants: | | | | | | | | | | | | | | |
| Avena fatua | 25 | 40 | 52 | 70 | 85 | 100 | 80 | 90 | 100 | 80 | 97 | 100 | 87 | 100 |
| Galium aparine | 17 | 24 | 35 | 45 | 62 | 100 | 100 | 100 | 100 | 100 | 100 | 100 | 100 | 100 |
| Matricaria chamomilla | 7 | 18 | 25 | 30 | 40 | 98 | 98 | 100 | 98 | 100 | 100 | 100 | 100 | 100 |

0 = no damage
100 = complete destruction

| Active ingredient | III+XIX | | | III+XX | | | VI+XVI | | | VI+XVIII | | |
|---|---|---|---|---|---|---|---|---|---|---|---|---|
| kg/ha | 0.5 / 1.5 | 1.5 / 0.5 | 1 / 1 | 0.5 / 1.5 | 1.5 / 0.5 | 1 / 1 | 0.5 / 1 | 1 / 0.5 | 0.75 / 0.75 | 0.5 / 1 | 1 / 0.5 | 0.75 / 0.75 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 75 | 100 | 100 | 82 | 97 | 87 | 75 | 85 | 98 | 80 | 92 |
| Galium aparine | 98 | 98 | 100 | 100 | 100 | 100 | 85 | 100 | 98 | 80 | 100 | 100 |
| Matricaria chamomilla | 98 | 100 | 100 | 98 | 100 | 100 | 85 | 100 | 100 | 90 | 100 | 100 |

0 = no damage
100 = complete destruction

| Active ingredient | VI+XVIII | | | VI+XIX | | | VI+XX | | | XVI+V | | |
|---|---|---|---|---|---|---|---|---|---|---|---|---|
| kg/ha | 0.5 | 1 | 0.75 | 0.5 | 1 | 0.75 | 0.5 | 1 | 0.75 | 0.5 | 1.5 | 1 |
|  | 1 | 0.5 | 0.75 | 1 | 0.5 | 0.75 | 1 | 0.5 | 0.75 | 1.5 | 0.5 | 1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 98 | 85 | 97 | 92 | 70 | 90 | 95 | 80 | 90 | 97 | 100 | 100 |
| Galium aparine | 87 | 100 | 100 | 80 | 98 | 86 | 80 | 100 | 90 | 80 | 90 | 85 |
| Matricaria chamomilla | 92 | 100 | 100 | 85 | 100 | 100 | 83 | 100 | 100 | 50 | 70 | 70 |

0 = no damage
100 = complete destruction

| Active ingredient | XVII+XII | | | XVIII+XII | | | XIX+XIII | | | XX+XIII | | |
|---|---|---|---|---|---|---|---|---|---|---|---|---|
| kg/ha | 0.5 | 1.5 | 1 | 0.5 | 1.5 | 1 | 0.5 | 1.5 | 1 | 0.5 | 1.5 | 1 |
|  | 1.5 | 0.5 | 1 | 1.5 | 0.5 | 1 | 1.5 | 0.5 | 1 | 1.5 | 0.5 | 1 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 100 | 100 | 100 | 100 | 100 | 100 | 100 | 100 | 100 | 100 | 100 |
| Galium aparine | 65 | 90 | 75 | 70 | 95 | 83 | 60 | 90 | 68 | 65 | 80 | 70 |
| Matricaria chamomilla | 58 | 75 | 70 | 60 | 80 | 80 | 60 | 70 | 75 | 60 | 80 | 75 |

0 = no damage
100 = complete destruction

| Active ingredient | III+XVI+V | | | III+XVII+XII | | | III+VIII+XIII | | | III+XIX+VI | | |
|---|---|---|---|---|---|---|---|---|---|---|---|---|
| kg/ha | 0.5 | 1 | 0.5 | 0.5 | 1 | 0.5 | 0.5 | 1 | 0.5 | 0.5 | 1 | 0.5 |
|  | 0.5 | 0.5 | 1 | 0.5 | 0.5 | 1 | 0.5 | 0.5 | 1 | 0.5 | 0.5 | 1 |
|  | 1 | 0.5 | 0.5 | 1 | 0.5 | 0.5 | 1 | 0.5 | 0.5 | 1 | 0.5 | 0.5 |
| Crop plants: | | | | | | | | | | | | |
| Beta vulgaris | 0 | 0 | 0 | 0 | 0 | 0 | 0 | 0 | 0 | 0 | 0 | 0 |
| Unwanted plants: | | | | | | | | | | | | |
| Avena fatua | 100 | 92 | 80 | 100 | 100 | 95 | 100 | 100 | 100 | 95 | 78 | 75 |
| Galium aparine | 90 | 90 | 95 | 90 | 75 | 97 | 90 | 80 | 95 | 97 | 100 | 95 |
| Matricaria chamomilla | 95 | 80 | 97 | 95 | 87 | 100 | 100 | 90 | 100 | 100 | 100 | 100 |

0 = no damage
100 = complete destruction

| Active ingredient | III+XX+XII | | | XVI+XII+VI | | | XVII+XIII+V | | | XVIII+VI+V | | | XX+XII+V | | |
|---|---|---|---|---|---|---|---|---|---|---|---|---|---|---|---|
| kg/ha | 0.5 | 1 | 0.5 | 0.5 | 1 | 0.5 | 0.5 | 1 | 0.5 | 0.5 | 1 | 0.5 | 0.5 | 1 | 0.5 |
|  | 0.5 | 0.5 | 1 | 0.5 | 0.5 | 1 | 0.5 | 0.5 | 1 | 0.5 | 0.5 | 1 | 0.5 | 0.5 | 1 |
|  | 1 | 0.5 | 0.5 | 1 | 0.5 | 0.5 | 1 | 0.5 | 0.5 | 1 | 0.5 | 0.5 | 1 | 0.5 | 0.5 |
| Crop plants: | | | | | | | | | | | | | | | |
| Beta vulgaris | 0 | 0 | 0 | 0 | 0 | 0 | 0 | 0 | 0 | 0 | 0 | 0 | 0 | 0 | 0 |
| Unwanted plants: | | | | | | | | | | | | | | | |
| Avena fatua | 100 | 100 | 95 | 100 | 95 | 100 | 100 | 100 | 100 | 97 | 100 | 100 | 100 | 100 | 100 |
| Galium aparine | 100 | 70 | 95 | 74 | 100 | 85 | 60 | 70 | 75 | 100 | 80 | 90 | 60 | 65 | 72 |
| Matricaria chamomilla | 100 | 85 | 98 | 80 | 100 | 90 | 62 | 65 | 80 | 100 | 80 | 92 | 60 | 58 | 75 |

0 = no damage
100 = complete destruction

I claim:

1. A herbicide composition consisting essentially of an inert carrier and a herbicidally effective amount of a mixture of a. a compound of the formula

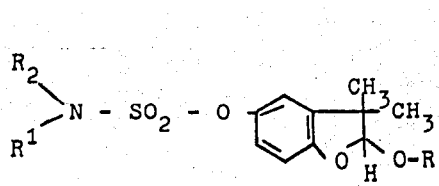

where R is methyl, ethyl, propyl, isopropyl, allyl or propargyl, $R^1$ is methyl and $R^2$ is hydrogen or methyl, and b. 1-phenyl-4-amino-5-chloropyridazone-(6) in a weight ratio of a to b in the range of 3:1 to 1:3.

2. A herbicide composition as claimed in claim 1 wherein compound a is 2,3-dihydro-3,3-dimethyl-2-ethoxybenzofuran-5-yldimethylamino sulfonate.

3. A herbicide composition as claimed in claim 1 wherein compound a is 2,3-dihydro-3,3-dimethyl-2-ethoxybenzofuran-5-yl monomethylamino sulfonate.

4. A herbicide composition as claimed in claim 1 wherein compound a is 2,3-dihydro-3,3-dimethyl-2-methoxybenzofuran-5-yldimethylamino sulfonate.

5. A herbicide composition as claimed in claim 1 wherein compound a is 2,3-dihydro-3,3-dimethyl-2-methoxybenzofuran-5-ylmethylamino sulfonate.

6. A herbicide composition as claimed in claim 1 wherein compound a is 2,3-dihydro-3,3-dimethyl-2-propoxybenzofuran-5-yldimethylamino sulfonate.

7. A herbicide composition as claimed in claim 1 wherein compound a is 2,3-dihydro-3,3-dimethyl-2-isopropoxybenzofuran-5-yldimethylamino sulfonate.

8. A herbicide composition as claimed in claim 1 wherein compound a is 2,3-dihydro-3,3-dimethyl-2-allyloxybenzofuran-5-ylmethylamino sulfonate.

9. A herbicide composition as claimed in claim 1 wherein compound a is 2,3-dihydro-3,3-dimethyl-2-propargyloxybenzofuran-5-ylmethylamino sulfonate.

10. A herbicide composition as claimed in claim 1 wherein compound a is 2,3-dihydro-3,3-dimethyl-2-allyloxybenzofuran-5-yldimethylamino sulfonate.

* * * * *